United States Patent [19]
Dolan et al.

[11] Patent Number: 5,985,153
[45] Date of Patent: Nov. 16, 1999

[54] MAGNETIC SEPARATION APPARATUS AND METHODS EMPLOYING AN INTERNAL MAGNETIC CAPTURE GRADIENT AND AN EXTERNAL TRANSPORT FORCE

[75] Inventors: Gerald J. Dolan, Philadelphia; Leon W. M. M. Terstappen, Huntingdon, both of Pa.

[73] Assignee: Immunivest Corporation, Wilmington, Del.

[21] Appl. No.: 08/867,009

[22] Filed: Jun. 2, 1997

Related U.S. Application Data

[60] Provisional application No. 60/019,282, Jun. 7, 1996, and provisional application No. 60/030,436, Nov. 5, 1996.

[51] Int. Cl.⁶ .......................... B01D 35/06; G01N 33/533
[52] U.S. Cl. ........................... 210/695; 210/94; 210/222; 210/745; 209/214; 209/223.1; 356/336; 435/7.2; 436/172; 436/177; 436/526
[58] Field of Search ...................................... 210/222, 695, 210/94, 745; 435/7.2, 7.9, 7.92; 436/10, 18, 172, 177, 526; 209/214, 223.1; 356/336

[56] References Cited

U.S. PATENT DOCUMENTS

| | | |
|---|---|---|
| 4,729,949 | 3/1988 | Weinreb et al. . |
| 4,735,504 | 4/1988 | Tycko . |
| 4,989,978 | 2/1991 | Groner . |
| 5,030,560 | 7/1991 | Sinor et al. . |
| 5,053,344 | 10/1991 | Zborowski et al. . |
| 5,200,084 | 4/1993 | Liberty et al. . |
| 5,340,749 | 8/1994 | Fujiwara et al. . |
| 5,375,606 | 12/1994 | Slezak et al. . |
| 5,411,863 | 5/1995 | Miltenyi . |
| 5,428,451 | 6/1995 | Lea et al. . |
| 5,451,525 | 9/1995 | Shenkin et al. . |
| 5,466,574 | 11/1995 | Liberti et al. . |
| 5,494,831 | 2/1996 | Kindler . |
| 5,498,550 | 3/1996 | Fujiwara et al. . |
| 5,541,072 | 7/1996 | Wang et al. . |

FOREIGN PATENT DOCUMENTS

| | | |
|---|---|---|
| WO9411078 | 5/1994 | WIPO . |
| WO9626782 | 9/1996 | WIPO . |

OTHER PUBLICATIONS

Chen, et al., "Automated Enumeration of CD34⁺ Cells in Peripheral Blood and Bone Marrow", J. of Hematotherapy; 3:3–13 (1994).

de Groth, et al., "The Cytodisk: A Cytometer Based Upon a New Principle of Cell Alignment", Cytometry; 6:226–233 (1995).

Kamentsky, et al., "Microscope–Based Muliparameter Laser Scanning Cytometer Yielding Data Comparable to Flow Cytometry Data", Cytometry; 12:381–387 (1991).

Stewart, et al., "Quantitation of Cell Concentration Using the Flow Cytometer", Cytometry; 2:238–243 (1982).

Takayasu, et al., "HGMS Studies of Blood Cell Behavior in Plasma", IEEE Transactions of Magnetics, 18:1520–1522 (1982).

Takayasu, et al., "High Gradient Magnetic Separation II. Single Wire Studies of Shale Oils", IEEE Transactions on Magnetics; 18:1695–1697 (1982).

Zwerner, et al., "A Whole Blood Alternative to Traditional Methods for CD4⁺ T Lymphocyte Determine" J. of Acquired immune Deficiency Syndromes and Human Retrovirology; 14:31–34 (1997).

*Primary Examiner*—David A. Reifsnyder
*Attorney, Agent, or Firm*—Dann, Dorfman, Herrell and Skillman

[57] ABSTRACT

The present invention relates to apparatus and methods for separating, immobilizing, and quantifying biological substances from within a fluid medium. Biological substances are observed by employing a high internal gradient magnetic capture structure formed within a vessel, in conjunction with an externally-applied force for transporting magnetically responsive material toward the capture structure. The invention is also useful in conducting quantitative analysis and sample preparation in conjunction with automated cell enumeration techniques.

28 Claims, 9 Drawing Sheets

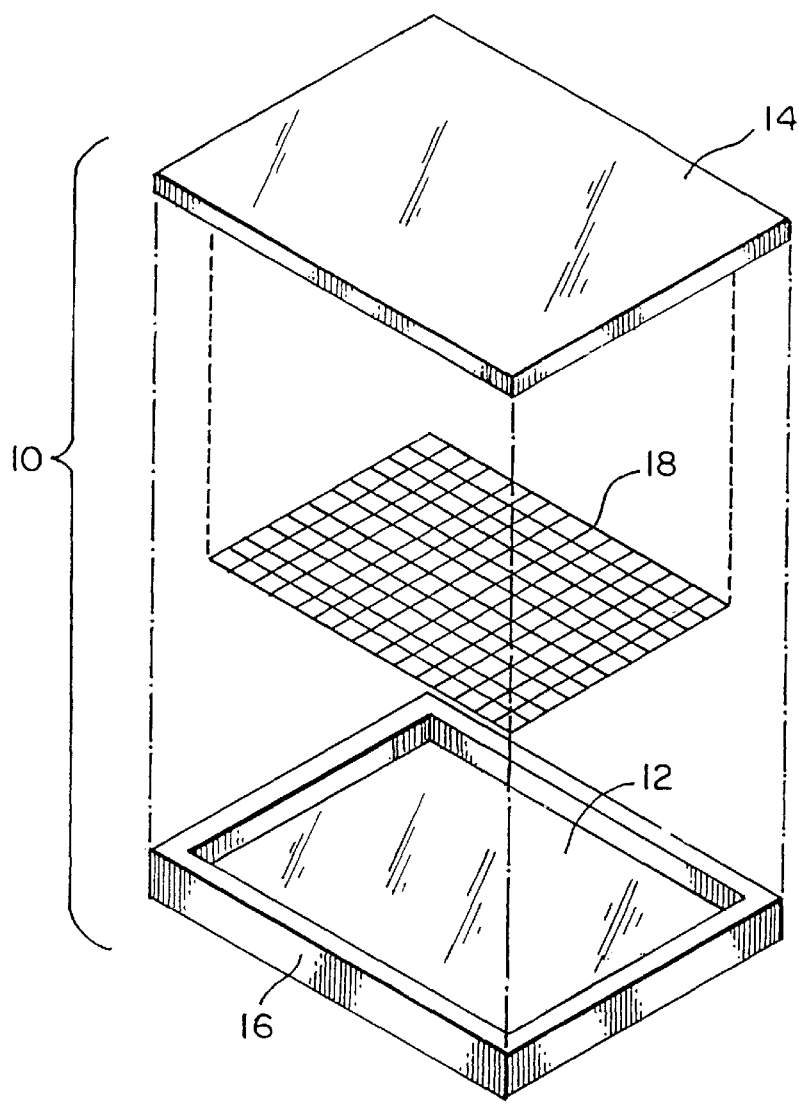
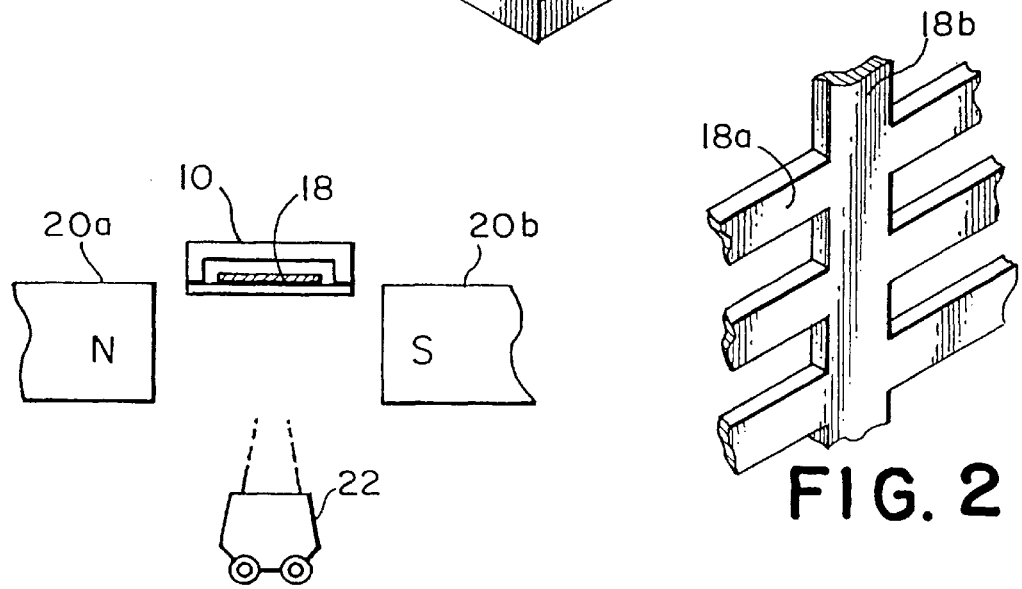

MAGNETIC SEPARATION APPARATUS AND METHODS EMPLOYING AN INTERNAL MAGNETIC CAPTURE GRADIENT AND AN EXTERNAL TRANSPORT FORCE

CROSS-REFERENCE TO RELATED APPLICATIONS

Priority is claimed herein to U.S. Provisional Application No. 60/019,282, filed Jun. 7, 1996, and to U.S. Provisional Application No. 60/030,436, filed Nov. 5, 1996, both of which are incorporated by reference herein.

FIELD OF THE INVENTION

The present invention relates to an apparatus and method for separating and immobilizing a magnetically responsive material from within a fluid medium. More particularly, the invention relates to an apparatus and method employing a high internal gradient magnetic capture structure formed within a vessel, in conjunction with an externally-applied force for transporting magnetically responsive material toward the capture structure.

BACKGROUND OF THE INVENTION

A magnetic material or magnetic dipole will move in a magnetic field gradient in the direction of increasing highest magnetic field strength. Magnetic gradients employed in fluid separations are broadly divided into two categories. Internal magnetic gradients are formed by inducing a magnetization in a susceptible material placed in the interior of a separation vessel. External gradients are formed by an externally positioned magnetic circuit.

In the case of a simple rectangular bar magnet, field lines which form from magnetic circuits conventionally move from North to South and are easily visualized with iron filings. From this familiar experiment in elementary physics it will be recalled that there is greater intensity of field lines nearest the poles. At the poles, the edges formed with the sides and faces of the bar will display an even greater density or gradient. Thus, a steel ball placed near a bar magnet is first attracted to the nearest pole and next moves to the region of highest field strength, typically the closest edge. For magnetic circuits, any configuration which promotes increased or decreased density of field lines will generate a gradient. Opposing magnet designs, such as N-S-N-S quadrupole arrangements having opposing North poles and opposing South poles, generate radial magnetic gradients.

Internal high gradient magnetic separators have been employed for nearly 50 years for removing weakly magnetic materials from slurries such as in the kaolin industry or for removing nanosized magnetic materials from solution. In an internal high gradient magnetic separator, a separation vessel is positioned in a uniform magnetic vessel. A ferromagnetic structure is positioned within the vessel in order to distort the magnetic field and to generate an "internal" gradient in the-field. Typically, magnetic grade stainless steel wool is packed in a column which is then placed in a uniform magnetic field which induces gradients on the steel wool as in U.S. Pat. No. 3,676,337 to Kolm. Gradients as high as 200 kGauss/cm are easily achieved. The magnitude of the field gradient in the vicinity of a wire is inversely related to the wire diameter. The spatial extent of the high gradient region is proportionally related to the diameter of the wire. As will be detailed below, collection of magnetic material takes place along the sides of the wire, perpendicular to the applied magnet field lines, but not on the sides tangent to the applied field. In using such a system, material to be separated is passed through the resulting magnetic "filter". Then, the collected material is washed, and the vessel is moved to a position outside the applied field, so that magnetic can be removed, making the collector ready for reuse.

Table I below indicates the magnitude of a magnetic gradient as a function of distance R, from the center of a ferromagnetic wire for round wires of different diameters. The gradients are determined by Maxwell's equations, which produce equations I and II for the strength of the magnetic field about the wires and the gradient of the field. The equations give the magnitude of these quantities when the wire has an internal magnetization per unit volume of M. If the wires are composed of "soft" ferromagnetic materials, the magnetization depends on the value, $B_{ext}$, of an externally applied field. For any value of M, even for a hard ferromagnetic material with constant, uniform magnetization, the dependence on the distance and wire diameter are as shown. The gradient values listed in Table 1 assume a typical wire magnetization such that $4\pi M=10$ kiloGauss (kG), a value close to that of a rare earth magnetic alloy. Table 1 demonstrates that for a narrower wire, the field gradient at the surface of the wire is larger than for thicker wires, although the magnitude of the gradient falls off much more rapidly with distance from the wire.

TABLE I

| | Diameter of wire | | | | |
|---|---|---|---|---|---|
| Distance from wire center (R) | 0.2 μm grad B (kG/cm) | 2.0 μm grad B (kG/cm) | 20 μm grad B (kG/cm) | 200 μm grad B (kG/cm) | 2000 μm grad B (kG/cm) |
| 0.1 μm | 600,000 | — | — | — | — |
| 0.2 μm | 75,000 | — | — | — | — |
| 0.5 μm | 4,800 | — | — | — | — |
| 1.0 μm | 600 | 60,000 | — | — | — |
| 2.0 μm | 75 | 7,500 | — | — | — |
| 5.0 μm | 4.8 | 480 | — | — | — |
| 10.0 μm | 0.6 | 60 | 6,000 | — | — |
| 20.0 μm | 0.075 | 7.5 | 750 | — | — |
| 50.0 μm | 0.0048 | 0.48 | 48 | — | — |
| 0.10 mm | 0.0006 | 0.06 | 6.0 | 600 | — |
| 0.20 mm | 0.000075 | 0.0075 | 0.75 | 75 | — |
| 0.50 mm | 0.0000048 | 0.00048 | 0.048 | 4.8 | — |
| 1.0 mm | — | 0.00006 | 0.006 | 0.6 | 60 |
| 2.0 mm | — | — | 0.00075 | 0.075 | 7.5 |
| 5.0 mm | — | — | 0.000048 | 0.0048 | 0.48 |

$$B_{int}=[B_{ext}(\mu-1)D^2]/[4(\mu+1)R^2]=2\pi M\ D^2/4R^2 \quad (I)$$

$$\text{grad } B_{int}=[B_{ext}(\mu-1)D^2]/[4(\mu+1)R^3]=2\pi M\ D^2/4R^3 \quad (II)$$

where

D=the diameter of a circular wire

R=the distance from the center of the wire

M=the wire magnetization $\mu$=the magnetic permeability of the wire $B_{ext}$=the magnitude of the external field perpendicular to the wire $B_{int}$=the magnitude of the resultant internal field contribution grad $B_{int}$=the magnitude of the resultant internal field gradient A method and apparatus for separating cells and other fragile particles are described by Graham, et al in U.S. Pat. No. 4,664,796. The apparatus contains a rectangular chamber within a cylinder. One pair of opposing sides of the chamber are made of non-magnetic material, while the other sides are made of magnetic material. The flow chamber is packed with a magnetically responsive interstitial separation matrix of steel wool. The material to be separated is run through the chamber, which is positioned in a uniform magnetic field. During separation, the chamber is aligned in the magnetic field such that the magnetic sides of the chamber are parallel to the applied field lines, thus inducing high gradients about the interstitial matrix in the chamber. When the chamber is in this position, magnetically labeled cells are attracted to the matrix and held thereon, while the non-magnetic components are eluted. The chamber is then rotated, so that the magnetic sides face magnets, which "shunts" or "short-circuits" the magnetic field, reclines the gradients in the flow chamber, and allows the particles of interest to be removed by the shearing force of the fluid flow.

Other internal magnetic separation devices are known. Commonly owned U.S. Pat. No. 5,200,084 teaches the use of thin ferromagnetic wires to collect magnetically labeled cells from solution. U.S. Pat. No. 5,411,863 to Miltenyi teaches the use of coated steel wool, or other magnetically susceptible material to separate cells. U.S. patent application Ser. No. 08/424,271 now abandoned by Liberti and Wang teaches an internal HGMS device useful for immobilization, observation, and performance of sequential reactions on cells.

External gradient magnetic separators are also known for collecting magnetically responsive particles. External devices are so-named because in such devices, a high gradient magnetic field is produced by a suitable configuration of magnets positioned external to the separation vessel, rather than by an internal magnetic structure. A standard bar magnet, for example, produces a gradient because the magnetic field lines follow non-linear paths and "fan out" or bulge along respective paths from North to South. Typical gradients of about 0.1 to 1.5 kGauss/cm are produced by high quality laboratory magnets. These relatively low gradients can be increased by configuring a magnetic circuit to compress or expand the field line density. For example, a second bar magnet positioned in opposition to a first magnet causes repulsion between the two magnets. The number of field lines remains the same, but they become compressed as the two magnets are moved closer together. Thus, an increased gradient results. Adding magnets of opposing field to this dipole configuration to form a quadrupole further increases the extent of the high gradient region. Other configurations, such as adjacent magnets of opposing fields, can be employed to create gradients higher than those caused by a bar magnet of equivalent strength. Another method of increasing gradients in external field devices is to vary the shapes of the pole faces or pole pieces. For example, a magnet having a pointed face causes an increased gradient relative to a magnet having a flat pole face.

U.S. Pat. No. 3,326,374 to Jones and U.S. Pat. No. 3,608,718 to Aubrey describe typical external gradient separators. Dipole configured separators for preventing scale and lime build up in water systems are described in U.S. Pat. No. 3,228,878 to Moody and U.S. Pat. No. 4,946,590 to Herzog. Adjacent magnets of opposing polarity have been used in drum or rotor separators for the separation of ferrous and non-ferrous scrap, as described in U.S. Pat. No. 4,869,811 to Wolanski et al. and U.S. Pat. No. 4,069,145 to Sommer et al.

External gradient devices have also been used in the fields of cell separation and immunoassay. U.S. Pat. Nos. 3,970,518 and 4,018,886 to Giaever describe the use of small magnetic particles to separate cells using an actuating coil. Dynal Corp. (Oslo, Norway) produces separators employing simple external magnetic fields to separate carrier beads for various types of cell separations. Commonly owned U.S. Pat. Nos. 5,466,574 and 5,541,072 disclose the use of external fields to separate cells for solution to form a monolayer of cells or other biological components on the wall of a separation vessel. Resuspension and recovery of the collected material usually requires removal of the collection vessel from the gradient field and some level of physical agitation. Turning now to the magnetic particles used in such collection devices, superparamagnetic materials have in the last 20 years become the backbone of magnetic separations technology in a variety of healthcare and bioprocessing applications. Such materials, ranging in size from 25 nm to 100 $\mu$m, have the property that they are only magnetic when placed in a magnetic field. Once the field is removed, they cease to be magnetic and can be redispersed into suspension. The basis for superparamagnetic behavior is that such materials contain magnetic cores smaller than 20–25 nm in diameter, which is estimated to be less than the size of a magnetic domain. A magnetic domain is the smallest volume for a permanent magnetic dipole to exist. Magnetically responsive particles can be formed about one or more such cores. The magnetic material of choice is magnetite, although other transition element oxides and mixtures thereof can be used.

Magnetic particles of the type described above have been used for various applications, particularly in health care, e.g. immunoassay, cell separation and molecular biology. Particles ranging from 2 $\mu$m to 5 gm are available from Dynal. These particles are composed of spherical polymeric materials into which magnetic crystallites have been deposited. These particles because of their magnetite content and size, are readily separated in relatively low external gradients (0.5 to 2 kGauss/cm). Another similar class of materials are particles manufactured by Rhone Poulenc which typically are produced in the 0.75 $\mu$m range. Because of their size, they separate more slowly than the Dynal beads in equivalent gradients. Another class of material is available from Advanced Magnetics. These particles are basically clusters of magnetite crystals, about 1 $\mu$m in size, which are coated with amino polymer silane to which bioreceptors can be coupled. These highly magnetic materials are easily separated in gradients as low as 0.5 kGauss/cm. Due to their size, both the Advanced Magnetics and Rhone Poulenc materials remain suspended in solution for hours at a time.

There is a class of magnetic material which has been applied to bioseparations which have characteristics which place them in a distinct category from those described above. These are nanosized colloids (see U.S. Pat. No. 4,452,773 to Molday; U.S. Pat. No. 4,795,698 to Owen, et al; U.S. Pat. No. 4,965,007 to Yudelson; U.S. Pat. No. 5,512,332 to Liberti & Piccoli; U.S. Pat. No. 5,597,531 to Liberti, et al and U.S. patent application Ser. No. 08/482,448 to Liberti, et al). They are typically composed of single to multi crystal agglomerates of magnetite coated with polymeric material which make them aqueous compatible. Individual crystals range in size from 8 to 15 nm. The coatings of these materials have sufficient interaction with solvent water to keep them permanently in a colloidal suspension. Typically, well coated materials below 150 nm will show no evidence of settling for as long as 6 months. These materials have substantially all the properties of ferrofluids.

Because of the small particle size and strong interaction with solvent water, substantial magnetic gradients are required to separate ferrofluids. It had been customary in the literature to use steel wool column arrangements described above which generate 100–200 kGauss/cm gradients. However, it was subsequently observed that such materials form "chains" (like beads on a string) in magnetic fields, thus allowing separation in gradient fields as low as 5 or 10 kGauss/cm. This observation led to development of separation devices using large gauge wires which generate relatively low gradients. Large gauge wires can be used to cause ferrofluids to produce uniform layers upon collection. By controlling amounts of ferrofluid in a system, a monolayer can be formed. Magnetically labeled cells can thus be made to form monolayers as described in commonly owned U.S. Pat. Nos. 5,186,827 and 5,466,574.

Analysis of the cellular composition of bodily fluids is used in the diagnosis of a variety of diseases. Microscopic examination of cells smeared or deposited on slides and stained by Romanowsky or cytochemical means has been the traditional method for cell analysis. Introduction of impedance based cell counters in the late 1950s has led to a major advance in the accuracy of cell enumeration and cell differentiation. Since then, various other technologies have been introduced for cell enumeration and differentiation such as Fluorescence Activated Flowcytometry, Quantitative Buffy Coat Analysis, Volumetric Capillary Cytometry and Laser Scanning Cytometry. Fluorescence based flowcytometry has improved the ability to discern different cell types in heterogeneous cell mixtures. Simultaneous assessment of multiple parameters of individual cells which pass a measurement orifice at a speed of up to 1,000 to 10,000 cells/sec is a powerful technology. However, there are limitations of the technology, such as an inability to analyze high cell concentration requiring dilution of blood, impracticability of detecting of infrequent or rare cells, and an inability to reexamine cells of interest. To overcome these limitations, clinical samples are typically subjected to various enrichment techniques such as erythrocyte lysis, density separation, immunospecific selection or depletion of cell populations prior to analysis by flowcytometry.

Many bioanalytical techniques involve identification and separation of target entities such as cells or microbes within a fluid medium such as bodily fluids, culture fluids or samples from the environment. It is also often desirable to maintain the target entity intact and/or viable upon separation in order to analyze, identify, or characterize the target entities. For example, to measure the absolute and relative number of cells in a specific subset of leukocytes in blood, a blood sample is drawn and incubated with a probe, for example a fluorescently labeled antibody specific for this subset. The sample is then diluted with a lysing buffer, optionally including a fixative solution, and the dilute sample is analyzed by flow cytometry. This procedure for analysis can be applied to many different antigens. However, the drawbacks to this procedure become apparent when large samples are required for relatively rare event analyses. In those situations, the time needed for the flow cytometer to analyze these samples becomes extremely long, making the analysis no longer feasible due to economic concerns.

One system which attempted to overcome some of the problems with flow cytometers was the so-called "Cytodisk," described in 1985 by DeGrooth, Geerken & Greve (Cytometry, 6: 226–233 (1985)). The authors describe a method of aligning cells in the grooves of a gramophone disk. The disk with dried cells was placed on a record player, and the arm of the record player was outfitted with an optical fiber immediately behind the needle. The needle kept the optical fiber aligned with the grooves in the record. The unicellular algae cells (3 microns in diameter) used in the reported experiment remained in the bottom of the groove, awaiting analysis by the optical system. The advantages of the Cytodisk included that cells could be subjected to multiparameter measurement with no optical cross-talk, individual cells could be indexed to said measurements, and cells could be measured repeatedly at different levels of analytical resolution. However, the system required that the cells be dried upon the gramophone record, a non-homogeneous process damaging to many cells. Even if cells were effectively dried upon the record for analysis, they would be dead cells. The current invention seeks to combine some of the benefits provided by the Cytodisk, including multiparameter measurement, indexing, and repeated measurement with new features which allow analysis of intact cells, which can be released for culturing or other re-use, including infusion back into a living organism.

SUMMARY OF THE INVENTION

This invention relates to the immobilization of microscopic entities, including biological entities, such as cells which enables separation of such entities from a fluid medium, including whole blood, into a defined region in a collection chamber, such that analysis by automated means is possible. This invention also provides for the quantitative collection of magnetically labeled target entities, such that microliter quantities of sample can be used to detect target entities, including those entities which occur at low frequencies.

In a preferred embodiment of the invention, a collection vessel is provided in which ferromagnetic lines are supported by adhesion along a transparent wall. The lines have effective diameters of 0.1 $\mu$m to 30 $\mu$m, resulting in immobilization and alignment of magnetically labeled biological materials in an ordered array. In a particularly preferred embodiment of the invention, human blood cells are aligned for automated analysis.

The methods of the invention employ dual forces for collecting particles. In one embodiment, target material is brought into range of the internal high gradient region by gravity. In another embodiment, a single applied magnetic field serves dual purposes. The applied field comprises a first, external magnetic gradient which moves magnetically responsive particles to a region of a collection vessel. At the same time, the applied field induces magnetization in a ferromagnetic collection structure, thereby adding a second, internal gradient which further acts upon the magnetically responsive particles to move them into defined region of the collection vessel for analysis. The vessel may be oriented such that the external gradient acts in opposition to, or in conjunction with, the influence of gravity upon the target material.

The methods of the invention have utility in the separation of biological entities which include a wide variety of substances of biological origins including cells, both eukaryotic (e.g. leukocytes, erythrocytes, platelets, epithelial cells, mesenchymal cells, or fungi) and prokaryotic (e.g. bacteria, protozoa or mycoplasma), viruses, cell components, such as organelles, vesicles, endosomes, lysosomal packages or nuclei, as well as molecules (e.g. proteins) and macromolecules (e.g. nucleic acids—RNA and DNA). The biological entities of interest may be present in at least samples or specimens of varying origins, including, biological fluids such as whole blood, serum, plasma, bone marrow, sputum, urine, cerebrospinal fluid, amniotic fluid or lavage fluids, as well as tissue homogenates, disaggregated tissue, or cell culture medium. They may also be present in material not having a clinical source, such as sludge, slurries, water (e.g.

ground water or streams), food products or other sources. The method of the invention also has utility in the separation of various bacteria and parasites from fecal matter, urine, or other sources.

BRIEF DESCRIPTION OF THE DRAWINGS

FIG. 1 is an exploded perspective view of a separation vessel according to one embodiment of the invention;

FIG. 2 is an enlarged perspective view of a ferromagnetic grid disposed in the separation vessel of FIG. 1;

FIG. 3 is a side elevational view of an arrangement for viewing collected cells in the separation vessel of FIG. 1;

DETAILED DESCRIPTION OF THE INVENTION

I. General Definitions

Figure 4A:
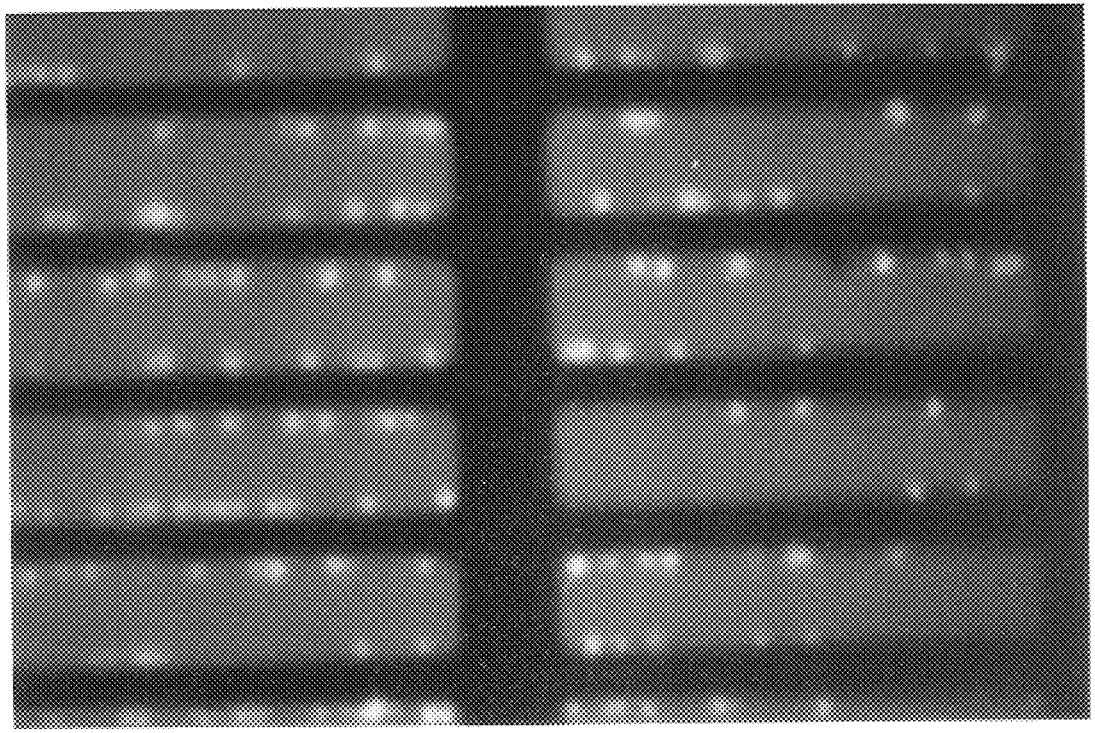
FIGS. 4A and 4B are photographs of cells collected in the arrangement of FIG. 3 under alternate methods of illumination.

Unless otherwise indicated, terms of general usage throughout the present specification are defined as follows.

The term "probe" as used herein refers to an antibody or other specific binding substance which contains or is adapted to include a detectable label. Detectable labels include fluorescent, chemiluminescent and radioactive compounds, as well as compounds which have distinct or recognizable lightscattering or other optical properties. Detectable labels also include those compounds which are only detectable upon binding to the characteristic determinant.

The term "ferromagnetic capture structure" as used herein refers to a structure of ferromagnetic material which becomes magnetized in the presence of a magnetic field to attract magnetically responsive particles. The capture structure may be provided in the form of wires, thin strips, lithographically formed strips, or electroplated ferromagnetic material supported on or by a wall of a separation vessel. The ferromagnetic material may include iron, nickel, cobalt, alloys of the same, alloys of magnetic rare earth elements, or other paramagnetic materials. The term "internal gradient" as used herein refers to a magnetic gradient induced by the capture structure when it is placed in a magnetic field. The term "external gradient" refers to a magnetic gradient applied solely by a configuration of magnets or pole pieces, external to the separation vessel. Electromagnets can also be used to form magnetic fields useful in the invention.

The term "determinant" is used here in a broad sense to denote that portion of the biological entity involved in and responsible for selective binding to a specific binding substance, the presence of which is required for selective binding to occur. The expression "characteristic determinant" is used herein in reference to cells, for example, to signify an epitope (or group of epitopes) that serve to identify a particular cell type and distinguish it from other cell types. Cell-associated determinants include, for example, components of the cell membrane, such as membrane-bound proteins or glycoproteins, including cell surface antigens of either host or viral origin, histocompatibility antigens or membrane receptors.

The expression "specific binding substance" as used herein refers to any substance that selectively recognizes and interacts with the characteristic determinant on a biological entity of interest, to substantial exclusion of determinants present on biological entities that are not of interest. Among the specific binding substances which may be used in affinity binding separations are antibodies, anti-haptens, lectins, peptides, peptide-nucleic acid conjugates, nucleic acids, Protein A, Protein G, concanavalin A, soybean agglutinin, hormones and growth factors. The term "antibody" as used herein includes immunoglobulins, monoclonal or polyclonal antibodies, immunoreactive immunoglobulin fragments, single chain antibodies, and peptides, oligonucleotides or any combination thereof which specifically recognize determinants with specificity similar to traditionally generated antibodies.

The term "magnetically responsive particles" as used herein refers to magnetic particles of metallic or organometallic composition, optionally coated with polymer, preferably coated with a polymer of biological origin such as BSA. The particles may be linked with an antibody or other specific binding substance to allow them to bind to biological entities of interest. Appropriate magnetic material is manufactured by Dynal, Rhone Poulenc, Miltenyi Biotec, Cardinal Associates, Bangs Labs, Ferrofluidics, and Immunicon Corp. Also included in the term "magnetically responsive particles" is a biological entity-magnetic particle complex, optionally bound to a fluorescent label or other detectable label.

The preferred magnetic particles for use in carrying out this invention are particles that behave as true colloids. Such particles are characterized by their sub-micron particle size, which is generally less than about 200 nanometers (nm), and their stability to gravitational separation from solution for extended periods of time. Such small particles facilitate observation of the target entities via optical microscopy since the particles are significantly smaller than the wavelength range of light. Suitable materials are composed of a crystalline core of superparamagnetic material surrounded by molecules which may be physically absorbed or covalently attached to the magnetic core and which confer stabilizing colloidal properties. The size of the colloidal particles is sufficiently small that they do not contain a complete magnetic domain, and their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Accordingly, colloidal magnetic particles are not readily separable from solution as such even with powerful electromagnets, but instead require a magnetic gradient to be generated within the test medium in which the particles are suspended in order to achieve separation of the discrete particles. Magnetic particles having the above-described properties can be prepared as described in U.S. Pat. Nos. 4,795,698, 5,512,332 and 5,597,531.

II. Gravitationally-Assisted Internal Gradient Immobilization

Referring now to FIG. 1, there is shown an exploded view of a separation vessel 10 according to a first embodiment of the invention. The vessel 10 comprises a pair of opposed parallel wall members 12 and 14 separated by perpendicular walls 16 defining an interior chamber. A ferromagnetic collection structure comprising a plurality of longitudinally extensive members is supported on and by an interior surface of the chamber. For example, a nickel mesh 18 is positioned upon the interior surface of the wall 14 and held thereon by an adhesive.

A portion of the mesh 18 is shown in FIG. 2. The mesh is formed by electroplating techniques, so that there are no interwoven or overlapping intersections that would undesirably entrap non-target substances by capillary attraction. Suitable meshes include nickel grids used in electron microscopy and are sold by Polysciences, Inc. of Warrington, Pa. (for example, catalog #8424N). The mesh comprises a plurality of longitudinal members 18a joined to cross members 18b forming a grid for mechanical support. The separation between the longitudinal members 18a should be at least twice the diameter of the particles desired to be collected. When the vessel 10 is positioned in a magnetic field transverse to the longitudinal members 18a, magnetically-labeled target material will be captured along both sides of each of the longitudinal members 18a. In order to form a monolayered linear array of the target particles along the interior surface of the wall 14 supporting the mesh 18, the height of the longitudinal members 18a should be no greater than the average diameter of the target entities. The number of target entities that may be captured in the vessel 10 is equal to twice the total length of the longitudinal members 18a divided by the average diameter of the target particles. The ferromagnetic collection structure, and hence the chamber, can thus be sized to permit collection of substantially all of the target entities expected to be present in a sample of test fluid.

EXAMPLE 1

Leukocyte Differentiation in Whole Blood

A vessel 10 was constructed having longitudinal members 18a extending 150 mm along a region of the wall 14 measuring 5 mm by 3 mm. The longitudinal members 18a were 5 μm in height, 20 μm wide, and separated by 63 μm spaces. The supporting members 18b were 48 μm wide. The height of the chamber was 0.13 mm, for a chamber volume of 2 μl. Hence, for collecting leukocytes, which have an average diameter of 10 μm, the particle collection capacity was 30,000. Such a collection capacity is sufficient for collecting substantially all leukocytes in the chamber volume.

A test fluid was prepared by adding 0.4 μg of a 130 nm CD45-labeled ferrofluid, 3 ng of acridine orange, and 10 ng of ethidium bromide to 1 μl of blood. The test fluid was allowed to incubate for 10 minutes, and deposited in the vessel 10. The vessel was then placed between a pair of magnets 20a and 20b, as shown in FIG. 3, with the mesh 18 positioned at the bottom of the chamber to allow the labeled cells to settle toward the mesh under the influence of gravity, and then to be aligned along the longitudinal members of the mesh in the internally-generated high gradient regions along the longitudinal members. To improve visibility of the captured material, the arrangement shown in FIG. 3 can then be inverted to allow the non-target material to settle away from the mesh 18.

Acridine orange is absorbed by the nucleated cells, which will emit green light when excited by blue light (460–500 nm). Under the same illumination, intracytoplasmatic granules of granulocytes will emit red light. Ethidium bromide is absorbed only by cells having non-intact membranes (i.e. dead cells), and will emit deep red light under blue illumination. The optical response of the material in the chamber to blue illumination was viewed through an inverted microscope 22. The resulting photographic image of FIG. 4A was obtained under a combination of blue illumination (permitting visibility of the fluorescence emitted from the captured cells) and ambient white illumination (permitting visibility of the ferromagnetic mesh). The captured fluorescent cells can easily be distinguished from other blood components.

Figure 4B:
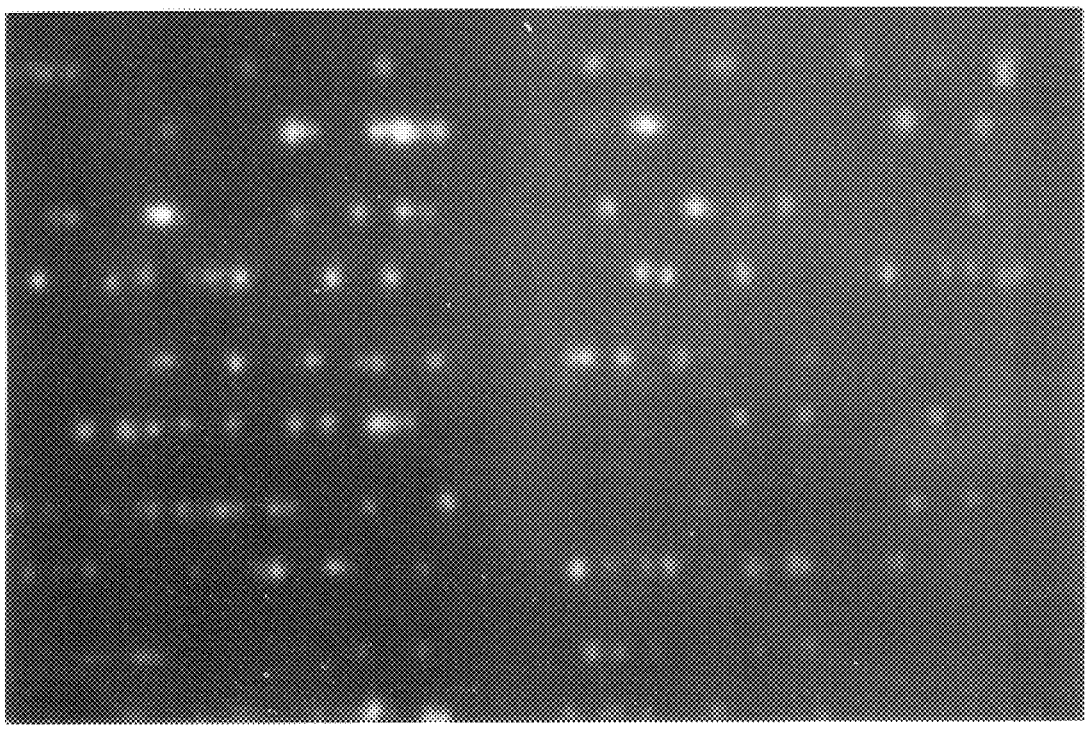

Discrimination between cell types can be achieved by detection of selected emission spectra and lightscatter properties of the collected cell. It will be apparent to those skilled in the art that probes with various specificities and different fluorescence excitation and emission can be used to differentiate between the captured, aligned cells. Also, one or more excitation wavelengths can be used to discriminate between the targets, or between the targets and the collection structure. For example, FIG. 4B shows the same collected cells under monochromatic blue fluorescent light. The collection structure is no longer easily visible, and the collected leukocytes are readily discernible. A standard microscope could then be used to observe the cells.

This example illustrates the differentiation of two types of cells. In this case, leukocytes were separated from other cell types and among the aligned leukocytes, live cells were discriminated from dead cells by the use of dyes. It will be apparent to one skilled in the art that any two (or more) cell types can be differentiated using different probes. For example: fetal nucleated red blood cells from maternal blood, circulating tumor cells (Epcam$^+$ CD45$^-$) from normal nucleated blood cells, platelets (CD41$^+$, PAC-1$^-$) from activated platelets (CD41$^+$, PAC-1$^+$), and various leukocyte subsets. Important leukocytes subsets found in human blood include CD4$^+$ or CD8$^+$ cells (T-lymphocyte cells); CD56$^+$ cells (NK cells); CD19$^+$ cells (B-lymphocytes); CD14$^+$ cells (monocytes); CD83$^+$ cells (dendritic cells); CD33$^+$, CD66a$^+$, or CD64$^+$ cells (granulocytes); CD66a$^+$CD66b$^+$ cells (activated granulocytes); CD34$^+$ cells)progenito4r cells); and CD90w$^+$ cells (hematopoietic stem cells)

EXAMPLE 2

Immunophenotypic Differentiation in Whole Blood

A blood sample is incubated with a fluorescent nucleic acid dye and ferrofluid labeled with an antibody directed against a cell surface epitope such as, for instance, CD4 expressed on T-helper lymphocytes and monocytes or CD34 present on progenitor cells. The incubation can take place in or outside the separation vessel. The vessel is then introduced into a magnetic field and the cells exhibiting the cell surface antigen recognized by the bioactive ferrofluid align on both sides of the ferromagnetic lines. Although all nucleated cells are fluorescently labeled, only those which are adjacent to the ferromagnetic lines are target cells and will be identified as such by an optical detection system arranged to scan for cells along the lines, as described further herein.

When the target cell frequency is low, as is the case for progenitor cells in peripheral blood identified by CD34 in normal donors (1–10 CD34+ cells/$\mu$l), the likelihood increases that non-target cells present by coincidence along the ferromagnetic lines will influence the accuracy of the enumeration. The likelihood that non-target cells are present by coincidence along a ferromagnetic line, and thus mistakenly enumerated as a target cell, can be reduced by decreasing the total length of the ferromagnetic lines. This can be achieved by decreasing the number of ferromagnetic lines in the chamber.

An alternative approach is not to use a fluorescent nucleic dye but to use a fluorescent labeled monoclonal antibody or other probes directed against the same cell type as the bioactive ferrofluid. Preferably this probe is directed against a different epitope as the bioactive ferrofluid. In this approach only the target cells are fluorescently labeled and identified as such. A drawback of the latter procedure is, however, that it requires a higher sensitivity of the detection system. Other labelling strategies include those generally used in flowcytometry and referred to as multi-color and/or multidimensional analysis. In this case, a bioactive ferrofluid is used to align the particles of interest along the ferromagnetic lines and a variety of monoclonal antibodies or other antigen specific probes labeled with different fluorochromes are used to identify different characteristics or populations within the immunomagnetically immobilized particles.

III. External Field-Aided Internal Gradient Immobilization

Separation methods according to a second embodiment of the invention employ both internally-generated and externally-applied magnetic gradients for collecting and immobilizing magnetically-responsive target substances. A non-uniform magnetic field is applied to a separation vessel. The external magnetic gradient moves magnetically responsive particles towards a ferromagnetic capture means. The applied magnetic field also induces magnetization of a ferromagnetic capture structure supported in the vessel. As the magnetically responsive particles move towards the ferromagnetic capture structure, they experience the additional influence of the internally-generated gradient, and are drawn toward the capture structure. If the capture structure is of an appropriate configuration, magnetically responsive particles are immobilized to align along the capture structure, and can be analyzed through a transparent wall of a chamber defined by the separation vessel. If the target material is appropriately labeled, fluorescence or light scattering can be measured through the wall to quantify the amount of target material in the test sample.

In a preferred embodiment of the invention, the applied magnetic field impels movement of the magnetically responsive particles against the force of gravity, providing an additional means of separation of labeled from unlabeled particles, thus reducing non-specific collection of particles.

Figure 5A:
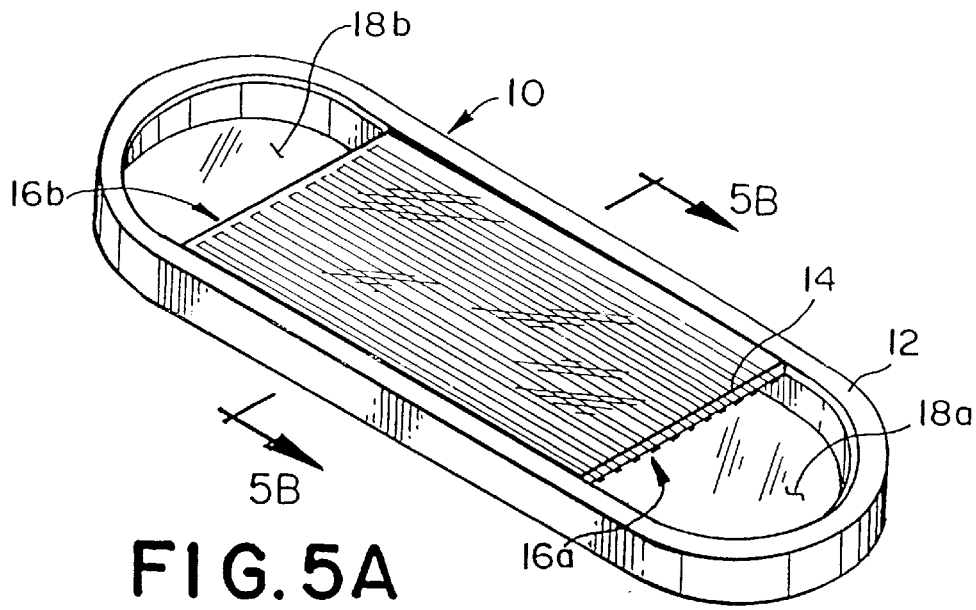
FIG. 5A is a perspective view of an alternative embodiment of a separation vessel containing a ferromagnetic capture structure according to the present invention.
Figure 5B:
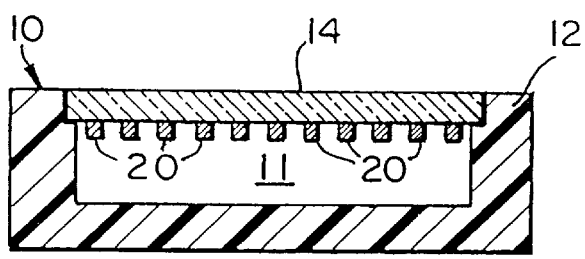
FIG. 5B is a sectional view of the separation vessel taken along the line 5B—5B of FIG. 5A.

Target substances labeled with the magnetically responsive colloidal particles described above can be collected in a collection vessel 10, shown in FIGS. 5A and 5B. The vessel 10 comprises a tub-shaped carrier member 12 having a recess formed therein, and a top wall member 14. The wall member 14 is configured to fit into the carrier member 12 to define a chamber 11 bounded by the interior surface of the wall member 14 and the interior surfaces of the carrier member 12. The wall member 14 is formed of a non-magnetic transparent material, such as glass, quartz or clear plastic. The carrier member 12 is also formed of a non-magnetic material, and is preferably also transparent.

The wall member 14 covers a portion of the recess formed in carrier member 12 to provide orifices 16a and 16b at opposed longitudinal ends of the chamber 11. The exposed recessed portions 18a and 18b of the carrier member 12 provide receptacles into which a drop of test fluid may be placed for analysis. Such a fluid may then flow into the chamber 11. Entry of fluid into the chamber 11 can be enhanced by capillary action, if the chamber is sufficiently narrow. Fiducial reference marks (not shown) may be formed or imprinted upon the wall member 14 to provide means for measuring the volume of fluid contained within the chamber 11.

A ferromagnetic collection structure is supported by adhesion or formed upon the interior surface of the wall member 14. In the embodiment shown in FIGS. 5A and 5B, the ferromagnetic collection structure comprises a plurality of lithographically-defined ferromagnetic lines 20 formed upon the interior surface of the wall member 14. The walls of the chamber 11 are optionally coated with a material such as BSA, silicone, or a negatively charged surface coating to provide chemically or biologically inert exposed interior surfaces. It is important to eliminate a buildup of electrostatic charge upon the wall surfaces to limit non-specific binding of target particles or free magnetic material to the walls of the chamber.

When the vessel 10 is placed into a magnetic field, the ferromagnetic lines 20 will become magnetized. The magnetic gradients produced by such lines 20 are comparable to the gradients calculated for a circular wire having the same cross-sectional area. The width of the ferromagnetic lines will not affect the monolayering of the particles along the magnetic lines, but the width does affect the strength of the magnetic gradient. The gaps between the lines 20 are preferably at least twice the diameter of the target particles. Optionally, a single line may be used for collection.

The thickness of the magnetic lines is chosen to be on the order of magnitude of the magnetically responsive target entities to be collected, so that the target entities will align along opposite sides 7 of the lines in a monolayer. Therefore, the lines 20 may be on the order of thickness of the particles to be collected. Preferably, the lines 20 are thinner than the diameter of the entities to be collected. If the entities to be collected are human lymphocytes on the order of 10 $\mu$m in diameter and the ferromagnetic lines 20 are about 5 $\mu$m thick, the cells will align in a single layer about 10 $\mu$m thick. It is particularly preferred for the magnetic lines to be significantly thinner than the diameter of particles to be collected. For example, magnetic lines on the order of 0.25 $\mu$m may be used to collect entities of 10 $\mu$m in diameter.

Such thin ferromagnetic lines can be manufactured by methods currently used in the manufacture of computer chips. In such a method, the surface of the wall member is first coated with a ferromagnetic material by a vapor deposition technique, such as vacuum evaporation or sputtering. Such a technique provides a layer of metal adhered to the eventual interior surface of the vessel. The combination of ferromagnetic material and the material used to form the wall member should be selected to provide sufficient adhesion of the ferromagnetic material to the wall member. A layer of photosensitive polymer, or photoresist, is then applied to the coated surface of the wall member and exposed to a pattern of ultraviolet light corresponding to the desired pattern of the ferromagnetic capture structure (or a negative image thereof, depending upon the photoresist employed). The photoresist is then developed to render undesired portions of the metal coating susceptible to removal by etching, such as wet chemical etching or reactive ion etching. Alternatively, the lines may be formed by a lift-off procedure wherein a photoresist pattern is first applied to the wall member and is removed subsequent to deposition of a ferromagnetic coating.

Such lithographic methods may be employed to produce a selected pattern of ferromagnetic metallization on a single wall member or upon a large-area substrate that is later to be divided into a plurality of wall members. These lithographic techniques can be substantially cheaper than the use of electroplating or electroforming, which would be used for thicker lines. Thin lines, by their nature, also tend to be smoother than their thicker counterparts. Such consistency is a by-product of the manufacturing technique. Smoother lines are important, because the induced magnetic fields are likewise more consistent. Since such small lines are being used, the strength of the magnetic field will vary greatly along a relatively "bumpy" line, which will lead to clumping of the collected magnetic material. Thus, a smoother ferromagnetic capture structure and more consistent magnetic fields will result in more evenly spaced magnetic material, facilitating automated examination of the collected material.

The separation of a magnetically responsive target substance, using the vessel 10, shall now be described in connection with various magnetic arrangements wherein an exemplary target substance shall be human lymphocytes labeled with magnetic particles manufactured as described in U.S. Pat. Nos. 4,795,698, 5,512,332 and 5,597,531 and in U.S. patent application Ser. No. 08/482,448 now U.S. Pat. No. 5,698,271, issued Dec. 16, 1997.

Figure 6:
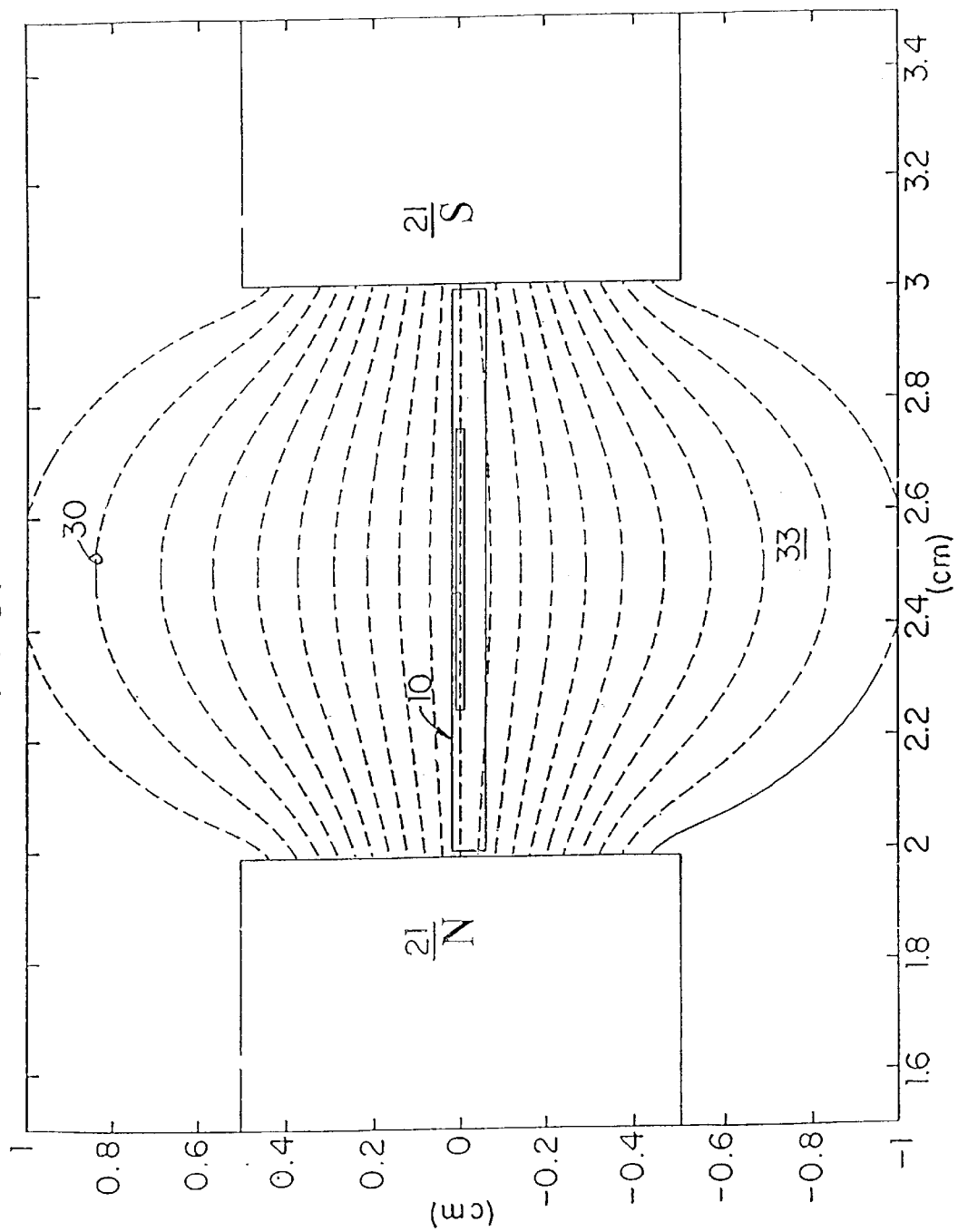
FIG. 6 is a schematic diagram of the separation vessel of FIG. 5A positioned in a relatively homogenous horizontal external magnetic field.

FIG. 6 shows the vessel 10 positioned in a substantially uniform magnetic field, shown by field lines 30, created in a gap between two magnets 21 of opposing polarity. For proper magnetization, the longitudinal axis of the ferromagnetic capture structure is oriented perpendicular to the field lines 30.

Figure 7:
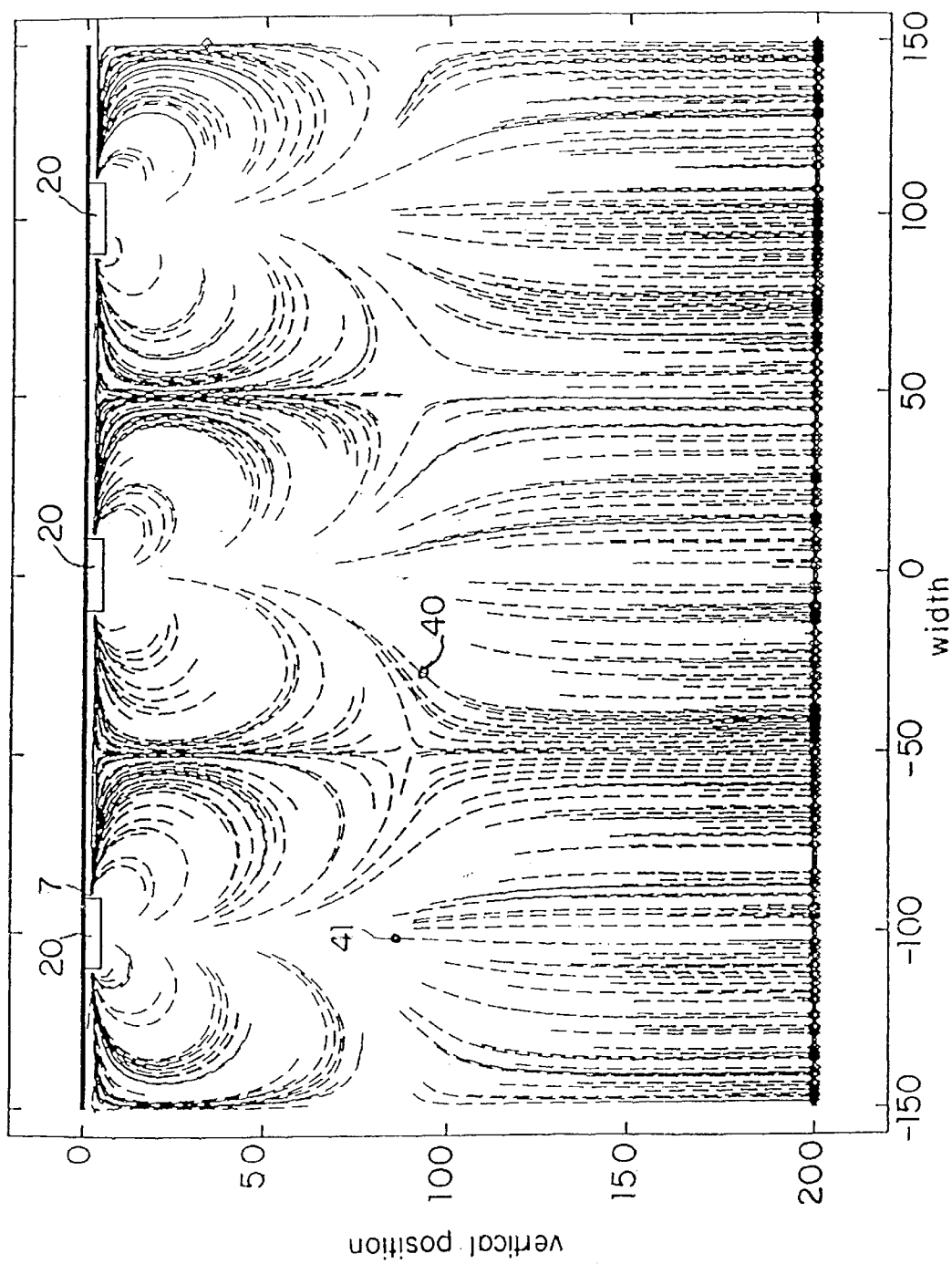
FIG. 7 is a computer generated diagram of the effect of the applied magnetic field of FIG. 6 upon movement of individual magnetically responsive particles disposed throughout the separation vessel.

FIG. 7 is a computer-generated diagram illustrating the paths 40 followed by numerous magnetically responsive particles 41 after the vessel is positioned in a homogeneous magnetic field. Magnetized ferromagnetic lines 20 with a thickness of 5 μm are shown end-on. A majority of particles in the chamber are unaffected by the internal magnetic gradients and eventually fall to the bottom of the chamber under the influence of gravity.

In the computer simulation employed to produce FIG. 7, all of the particles in the chamber were assumed to be magnetically responsive. In an actual separation, the majority of cells will not be magnetically responsive, and will thus settle to the bottom of the chamber under the influence of gravity. The relatively few target cells will collect in respective linear monolayers along the ferromagnetic lines.

In order to obtain quantitative information about the target particles, a reproducible and high percentage of the particles would desirably be collected by the device. In order to obtain information about relatively rare events, such as circulating tumor cells, fetal cells in maternal blood, or hematopoietic stem cells, virtually all target particles must be collected. In order to use relatively thin ferromagnetic structures to obtain alignment of the particles, a method of "sweeping up" the cells in the chamber is necessary to move the particles into the spatially limited internal high gradient regions. One way of "sweeping up" particles would be to use a narrow chamber. As indicated in FIG. 7, a chamber thickness of just under 100 μm is sufficient for 5 μm ferromagnetic lines, but this would require a small chamber volume, which would limit the opportunity to observe rare species. Using a long chamber to increase volume would require a longer ferromagnetic capture structure, and would increase the time needed to search along the capture structure for the collected target material. One could alternatively turn the chamber upside-down, such that gravity would assist to settle all particles upon the wires as described above in connection with the first embodiment. However, in fluids having a heterogeneous population dominated by non-target species, magnetically labeled material may not be able to move through a thick layer of settled non-target material to reach the ferromagnetic capture structure, resulting in loss of selectivity and crowding of the detection area. Another approach would be to increase the field strength of the magnets, but as shown in formula II, to double the range of the gradient, one would have to increase the external field strength eight-fold.

One method of the instant invention uses a non-uniform applied magnetic field to magnetize the ferromagnetic capture structure and also to provide an external gradient perpendicular to the capture structure "sweep up" the magnetically responsive particles not initially located within the influence of the internal magnetic gradients. The applied magnetic field preferably supplies an external gradient of sufficient magnitude to transport the cells towards the ferromagnetic capture structure where they are then immobilized against the wall adjacent the capture structure by the internal magnetic gradient. Attributes of such a field include that it is substantially homogeneous within a plane parallel to the ferromagnetic capture structure, and that the field is oriented perpendicular to the horizontal longitudinal axis of the structure. Additionally, the field includes a vertical external gradient component that increases in the direction toward the capture structure, and that the external gradient is high enough to transport magnetically-labeled material toward the capture structure. A magnetic field which could serve such dual purposes can be produced by various configurations of magnets. One advantageous arrangement of external source magnets is shown in FIG. 8.

Figure 8:
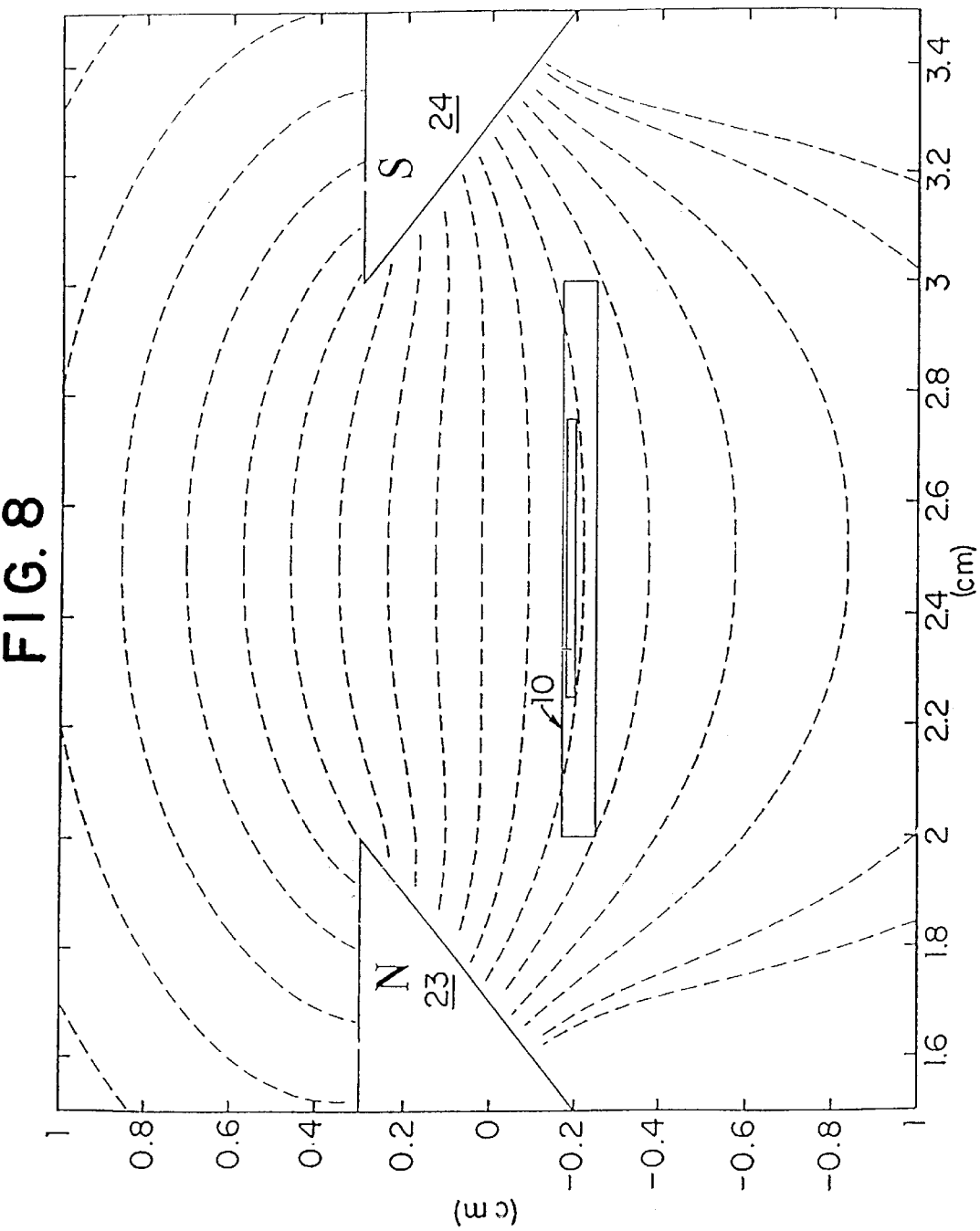
FIG. 8 is a schematic diagram of the separation vessel positioned in an applied field having an external gradient.

FIG. 8 shows the separation vessel 10 positioned at a preferred location relative to a pair of opposed magnetic poles 23 and 24 having a gap formed therebetween. The lower surfaces of the poles 23 and 24 are tapered toward the gap, so that the magnetic field applied to the chamber is non-uniform, and has a substantially vertical gradient effective to urge magnetically-responsive particles within the chamber against the force of gravity toward the ferromagnetic collection structure on the upper wall.

Figure 9:
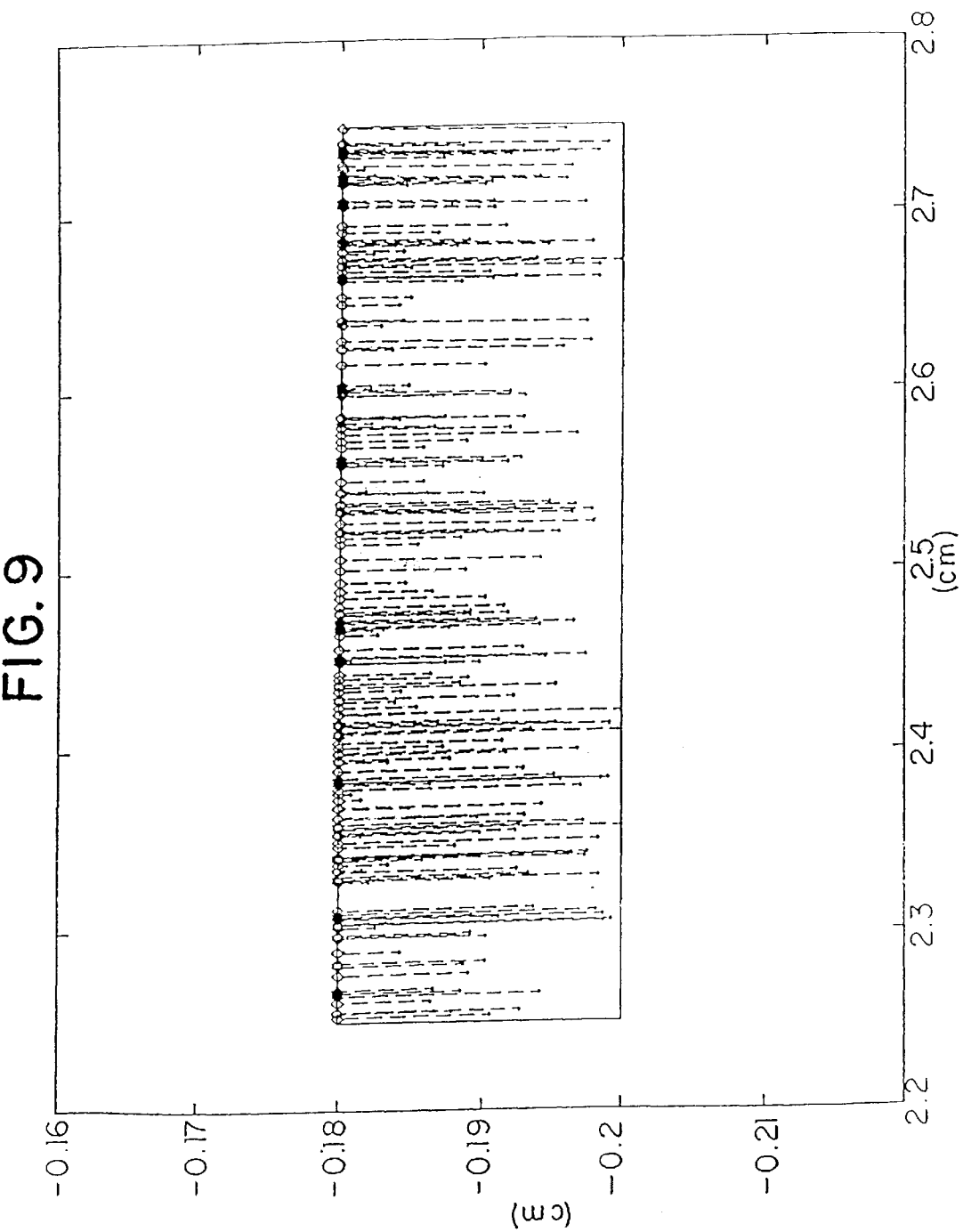
FIG. 9 is a computer generated diagram of the path component of numerous magnetically responsive particles in the separator of FIG. 8 due solely to the external gradient.

FIG. 9 shows the paths that would be followed by such particles within the chamber in the absence of the ferromagnetic collection structure. As can be seen, the influence of the externally-applied gradient is sufficient to move the particles substantially vertically toward the upper wall of the chamber.

Figure 10:
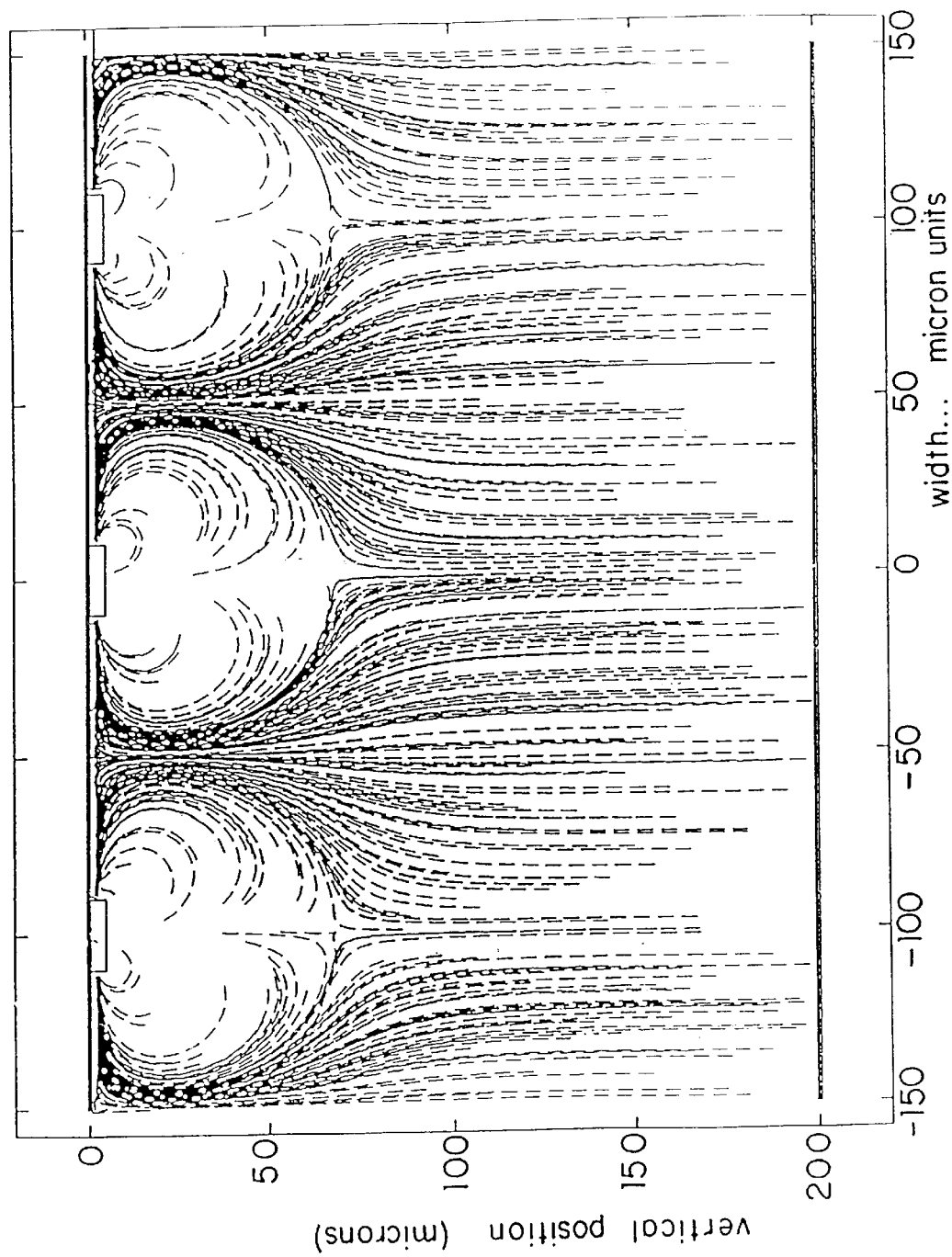
FIG. 10 is a computer generated diagram of the paths followed by magnetically responsive particles in the separation vessel of FIG. 8, taking into account the external gradient, the internal gradient, and gravity.

FIG. 10 shows the paths followed by particles within the chamber, including the effect thereon caused by the presence of a ferromagnetic collection structure comprising lithographically-defined lines having a thickness of 5.0 μm and a width of 20 μm. As can be seen, the externally applied gradient tends to urge particles initially located in the lower portion of the chamber to move into the high gradient regions generated by magnetization of the ferromagnetic lines.

Figure 11:
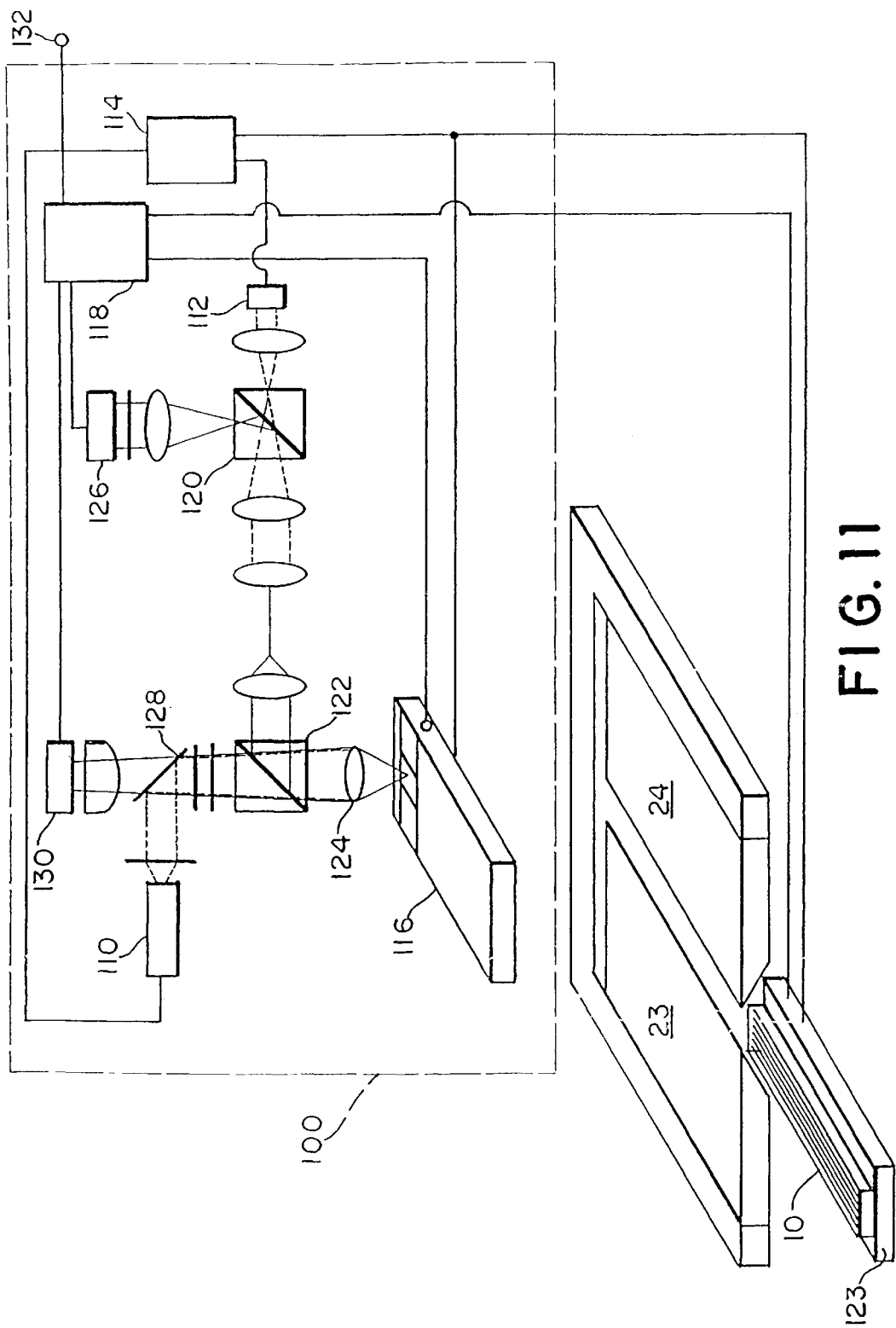
FIG. 11 is a schematic diagram an arrangement for automated analysis of collected target entities within a separation vessel of the type shown in FIG. 5A.

The precise design parameters for the magnets 23 and 24 shown in FIG. 8 (and shown in connection with an automated observation system in FIG. 11) required to induce a desirably strong internal gradient and to apply a desirably strong vertical external gradient, will depend upon application-specific conditions such as the magnetization of the magnetic particles employed, the mass and size of the target entities, and the viscosity and temperature of the fluid medium. Those skilled in the art will be enabled hereby to select appropriate design parameters in view of such considerations. In experimental conditions such as are described herein, a pair of rare earth magnets (Crucible Magnets; Elizabethtown, Ky.) having an internal magnetization of 1200 gauss and an acute taper angle of 20° separated by a distance of 5.0 mm to form a gap through which observations of collected entities could be made. The upper surface of the separation vessel was positioned 2.0 to 3.0 mm below the gap. Although FIG. 10 shows a chamber height of 200 $\mu$m, chamber heights of 1 mm have been modeled and actually used to collect and quantify magnetically labeled cells.

Of course, it is possible to exceed the capacity of the magnetic lines by attempting to collect so much target material, that a monolayer of target particles is no longer possible. In which case, the dilution of the test sample or the use of a larger chamber with a greater linear capacity of the magnetic lines is required.

Thus, analysis of the magnetically labeled target material is enabled. Alignment of the target material in a monolayer also allows for the analysis to be conducted by automated means, such as mechanical automated cell counting technology. The target material can be illuminated through the transparent wall member and the optical properties of the target material can be detected. Optical properties include the direct observation of the target material and the measurement of adsorbed, scattered or fluorescent light. Optionally, the target material can be analyzed aided by the addition of a substrate or other compound. Other compounds include the use of probes which recognize a characteristic determinant of the target material, and nuclear, cytoplasmic or membrane dyes. These probes can be either inherently fluorescent, fluorescently tagged, or fluorescent only upon binding to the characteristic determinant. Differentiation of the target material, i.e., leukocytes, is thus possible with a specific binding substance which recognizes subsets of the target material.

Although the above descriptions are exemplified by the collection of leukocytes, it is also possible to immobilize other types of cells in the apparat6us of the invention. For example, platelets can be selected by use of CD41 or CD61. Differentiation into subsets includes an analysis of their activation status (recognition by CD62p or PAC-1) or the presence of granules (recognition by CD63 or LDS-751). The immobilization of red blood cells is discussed elsewhere in this specification.

A notable advantage of the apparatus and method of the invention is that the ability to provide linearly monolayered entities presents the opportunity to perform sequential reactions in a rapid and highly efficient manner. Thus, not only can the apparatus and method of the invention be used to facilitate cell analysis for the determination of cell surface characteristics, e.g., T-Cell, B-Cell Progenitor cells and subset markers thereof, but they can in principle be applied for the analysis of intracellular components or genes. Such an analysis would be done by first capturing and aligning the cells of interest. This step would be followed by a series of sequential flow-by reactions, which would permeate the cell membrane, tag entities of interest and amplify signal on tagged entities. This capability provides a distinct advantage over existing cytometric technologies.

The following examples further describe aspects of the present invention.

EXAMPLE 3

A direct coated ferrofluid was prepared according to U.S. patent application Ser. No. 08/482,448. The ferrofluid particles were coated with CD45 antibody, which binds to leukocytes. The ferrofluid was stored in a HEPES buffer, pH 7.5 at 100 $\mu$g/ml.

The target cells were CEM cells at a concentration of $5 \times 10^6$ cell/ml. 100 $\mu$l of cells were incubated with 10–30 $\mu$l of ferrofluid for ten minutes at room temperature before loading the collection chamber.

A separation vessel was provided with a chamber having dimensions of 0.1 mm×5 mm×20 mm, for a chamber volume of 10 $\mu$l. The ferromagnetic capture structure comprised lithographically formed lines of nickel having dimensions of approximately 5 $\mu$m thick×25 $\mu$m wide. The lines were spaced at 100 $\mu$m intervals.

After incubation, approximately 10 $\mu$l of the magnetically labeled CEM cells were loaded into the collection chamber. The interior of the chamber was first observed in the absence of a magnetic field and almost all of the cells were observed to have settled at the bottom of the chamber. The chamber was then agitated to resuspend the cells. Then, the collection chamber was placed into a magnetic field formed by two square magnets (such as the magnets shows in FIG. 2). The vessel was located in a non-uniform region of the field outside of the substantially uniform field directly between the magnets (i.e., at the location 33 shown in FIG. 6). Hence, an external gradient in the vertical direction was applied to the chamber to urge the magnetically responsive particles toward the ferromagnetic capture means.

While the collection chamber was positioned in the magnetic field, it was supported upon a microscope stage for observation of the cells were through a transparent wall of the chamber. Almost all of the target cells were observed to be aligned along the ferromagnetic capture lines in a single layer. Most of the cells were observed to be aligned after about ten seconds after the chamber was placed in the magnetic field. After a minute, all discernible cell movement ceased.

In another experiment, the loaded chamber was placed in a substantially homogenous magnetic field as indicated by the chamber 10 shown in FIG. 6. Although the magnetized wires collected approximately 50% of the magnetically labeled CEM cells, a large number of cells settled to the bottom of the collection chamber.

EXAMPLE 4

The experiment of Example 3 was repeated with human whole blood. 100 $\mu$l of whole blood was incubated with 10–30 $\mu$l of the CD45 direct labeled ferrofluid described in example 1. After a ten minute incubation at room temperature, the collection chamber was loaded with 10 $\mu$l of test sample and positioned in the magnet arrangement described above. A short settling period of one minute was required to allow the non-target red cells to settle to the bottom of the chamber and away from the ferromagnetic capture means to allow observation of the target leukocytes cells. Upon microscopic examination, the target cells were seen to be aligned along upon the ferromagnetic capture lines. In other experiments with fluorescently labeled nucleated cells, no settling period was required to distinctly identify the collected target cells (i.e. leukocytes).

Although this example illustrated the alignment of leukocytes in whole blood, it is possible to further distinguish or differentiate the leukocytes with the addition of probes to the desired subpopulations of leukocytes. As noted in example 1, it will be apparent to one skilled in the art that the method described in this example could be applied to numerous types of cell separation and/or differentiation.

EXAMPLE 5

The instant invention should also be useful for conducting competitive immunoassays. Proteins, hormones, or other blood components may be measured in whole blood using a device similar to that described in connection with FIGS. 1A and 1B. Magnetic particles which directly or indirectly bind to the blood components to be analyzed could be introduced into a blood sample, along with a fluorescent, chemiluminescent or other detectable probe, which binds directly or indirectly with the component to be analyzed. After the solution containing the blood, magnetically responsive particle, and detectable probe has been introduced into the device, the device is placed into a non-uniform magnetic field, and oriented such that gravity and the externally applied gradient act together to reinforce each other, instead of acting in opposition. The magnetically labeled protein, hormone, or other blood component will be drawn down to the magnetic collection structure. The excess detectable probe would remain in solution. The cellular components in the blood would also be drawn down towards the magnetic collection structure due to gravity. Detection of the non-bound detectable probe through fluorescence emission, chemiluminescence, or other means would be possible through a transparent wall of the collection device. The probe's signal, such as light emission, from the non-bound detectable probe would initially be blocked by cells, such red blood cells. Such cells would eventually settle to form a layer over the magnetic collection structure(s) to allow unobstructed detection of an emission fluorescence, or light scattering probe signal.

III. Automated Optical Analysis of Immobilized Target Entities

As noted above in connection with FIG. 6, the fringing field beneath a pair of opposed rectangular cross-section magnets is capable of providing the desired vertical external gradient while inducing internal magnetization of the ferromagnetic collection structure. For microscopic observation of the collected material, wherein the optical observation system is limited by a finite focal length such as less than 5 mm, it is desirable to reduce the vertical distance between the top wall of the collection vessel and the top of the magnetic elements providing the field. In general, such an objective can be achieved in a magnetic arrangement having two opposing pole faces separated by a gap, wherein the pole faces are formed to have tapering surfaces toward the gap, such as shown in FIG. 8.

Providing a desirably short distance between the top of the magnetic arrangement and the top of the vessel permits the use of various automated observation means. Additionally, because target entities are collected in an orderly pattern on the interior surface of a transparent chamber, an automated observation system can be configured to provide relative motion between the vessel and the light gathering elements of the observation system in order to "track" the collected target entities for automated enumeration, which can include spectral analysis of light emitted or absorbed by the collected targets.

One such automated analysis system 100 is shown in FIG. 11. The analysis system 100 comprises optical tracking and beam analysis components similar to those employed for reading compact discs known in the audio and data storage arts. Briefly, a pair of laser diodes 110 and 112 are connected with a power supply 114 to generate respective parallel beams of light. One beam is employed by the analysis system for locating and tracking lines of the ferromagnetic collection structure. The other beam is used for detecting the presence of collected target entities adjacent to a located line. Relative motion between the optical elements of the analysis system 100 is provided by a mechanical tracking unit 116. Coordination of the functions of the analysis system 100 is provided by a microprocessor 118.

Laser 112 generates the tracking beam, which is transmitted through dichroic mirrors 120 and 122, and focussed upon the upper interior surface of the separation vessel 10 by objective lens 124. The tracking beam is reflected from the interior surface of the separation vessel, and is re-transmitted through dichroic mirrors 122 and 120 toward a photodetector 126. Photodetector 126 generates an electric signal in response to receiving the reflected light, which is provided to the microprocessor 118. The mechanical tracking unit 116 is operated by the microprocessor 118 to move the objective in the presumed direction of the lines of the ferromagnetic collection structure. Microprocessor 118 is programmed to detect deviations within the electrical signal from photodetector 126 to provide a feedback signal to the mechanical tracking unit 116 for adjusting the position of the objective 124 in a direction perpendicular to the lines of the ferromagnetic collection structure.

As the objective is moved to track the lines of the ferromagnetic collection structure, laser 110 is operated to generate a beam of light for detecting the presence of collected target entities. The light from laser 110 is transmitted through dichroic mirrors 128 and 122, and is focussed upon the upper interior surface of the collection vessel to form a spot adjacent to the focal point of the tracking beam. Light reflected by target entities will be transmitted through dichroic mirrors 122 and 128 toward photodetector 130. Photodetector 130 generates an electrical signal representative of the light reflected from the target entities, which is transmitted to microprocessor 118. Microprocessor 118 is programmed to monitor variations in the electrical signal from photodetector 130, in order to provide an analysis output signal, such as a counting signal at an output terminal 132. It will be appreciated that such an output signal can be further processed to provide information relative to the quantity and respective positions of the collected target entities.

In alternative embodiments, one laser could be used to illuminate the chamber, instead of two lasers as depicted in the analysis system 100. Optionally, the laser could be eliminated entirely and the chamber could be illuminated with a light-emitting diode or other light source, including light sources that illuminate the chamber from the sides or from below. In other embodiments, spectral analysis components, such as optical filters and gratings, as well as illuminating components having various spectral characteristics, can be employed in an automated analysis system for conducting spectral analysis of light emitted from the collected entities as an objective lens of the analysis system is moved to track the ferromagnetic collection structure.

In some cases, it may be desirable to include means to vibrate the chamber, to prevent magnetic particles from being held by friction against the walls of the chamber.

Vibrating the chamber has been found to increase magnetic separation efficiency under such circumstances. To facilitate vibration, the separation vessel may be mounted on a piezoelectric crystal 123 connected to an electric power source for vibrating the chamber at a desired frequency.

IV. Quantitative Determinations of Biological Fluid Components

A. Rare Species Enrichment and Sample Preparation

With decreasing frequency of a target population it becomes increasingly more difficult to reliably detect, enumerate and examine the target population. Not only is there an increasing demand on the specificity of the identifiers, i.e., probes or a combination of probes, but the need arises for a specific target enrichment technique in addition to the need to process larger volumes of the bodily fluid. Table II below illustrates this by showing the frequencies of various cell populations among the nucleated cells in peripheral blood of normal individuals.

TABLE II

| Cell Frequency | Cell Number | Targets Cells |
| --- | --- | --- |
| 1:1–1:10 | 10,000–1,000/$\mu$l | granulocytes, lymphocytes |
| 1:10–1:$10^2$ | 1,000–100/$\mu$l | monocytes, eosinophils |
| 1:$10^2$–1:$10^3$ | 100–10/$\mu$l | basophils |
| 1:$10^3$–1:$10^4$ | 10–1/$\mu$l | CD34+ cells |
| 1:$10^4$–1:$10^5$ | 1,000–100/ml | CD34+, CD38– cells |
| 1:$10^5$–1:$10^6$ | 100–10/ml | tumor cells |
| 1:$10^6$–1:$10^7$ | 10–1/ml | tumor cells |
| 1:$10^7$–1:$10^8$ | 1,000–100/l | tumor cells |

For analysis of infrequent cells, such as CD34+ cells or a subset thereof, or in case of disease potential circulating tumor cells, the amount of blood needed to reliably detect, enumerate and examine the target population needs to be substantially larger than 1 $\mu$l. One practical implication for the analysis of larger blood volumes is a substantially longer processing time. For example, for flow cytometric analysis of a 1 ml blood sample the erythrocytes in the sample are typically lysed, which is accompanied with a 10 fold dilution of the sample. For a typical sample flow rate of 1 $\mu$l/sec, the 10 ml volume of the lysed sample will thus require 2.78 hours for analysis. The need for enrichment of the target population and an increase in its concentration is thus clearly desired. A variety of enrichment methods can be employed to increase the concentration of the desired target in the sample to be analyzed, so that a sufficient number of target entities will be present in the separation vessel to permit detection. Success of these procedures is determined by carry over of non targets, recovery of targets, the ability to concentrate the target and the ability to accurately analyze the target after the procedure. Introduction into a separation vessel of a sample from a bodily fluid of which targets are concentrated and non targets are reduced, permits enumeration and examination of the target population. In one method of sample preparation, an external gradient separator of the type described in U.S. Pat. No. 5,186,827 may be employed. For example, to a vessel containing 10 ml of blood, a bioactive ferrofluid is added which identifies cells of epithelial origin. After appropriate incubation, the sample is placed in the external gradient separator. After separation, the blood components not magnetically attached to the wall of the vessel are removed while the desired target substance remains adhered to the wall of the separator. The separated cells can now be resuspended into a smaller volume when the separation vessel is removed from the magnetic field. To the resuspended sample, fluorescent labeled probes can be added. After incubation, the sample is again placed in an external gradient magnetic separator. After separation, the supernatant (including excess reagents) is removed, and the separated cells are resuspended in a volume commensurate with the chamber of a separation vessel of the present invention. Assuming the 10 ml of blood contained $10^8$ cells, a carryover of 0.01% would result in $10^4$ cells, which is within the range of the cell capture capacity of the apparatus of this invention. Given a target cell frequency of 1 in $10^7$ and a capture efficiency of 70%, 7 target cells would be captured, which is sufficient for identification and further characterization. The cells which express the antigen targeted by the ferrofluid will align along the ferromagnetic lines in addition to other cells which are nonspecifically bound to the ferrofluid. Cells which were captured due to other reasons, such as entrapment, will not align, resulting in a further purification of infrequent cell types. Identification and further characterization of the target cells can be obtained by the differences in the scattered and spectrum of the fluorescence light. An additional improvement can be achieved by utilization of a fluorescent form of the bioactive ferrofluid, the target cells can then be discriminated from non specifically bound cells by the amount of fluorescence emitted by the cells, i.e. the density of the antigen on the cell surface of the target cell is most likely different from the density of nonspecifically bound ferrofluid to non target cells. In contrast with flowcytometry the individual targets isolated by means of the present invention can be reexamined, in that an optical detection system can be configured to identify and record the location of the target particles of interest. Once the location of the target cells has been detected and recorded, the immobilization vessel then can be examined by a more sophisticated optical detection system, such as a confocal microscope.

B. Quantitative Analysis

For conducting quantitative analysis of certain cell types, a difficulty arises from having to perform multiple dilutions of the original blood sample prior to magnetically capturing the cell type of interest. After having performed multiple dilutions, determining the concentration of the captured species relative to the original blood volume requires knowledge of the precise dilution ratio and the magnetic capture efficiency. These quantities can be determined by adding concentration markers to the original blood sample.

A first marker, for determining the dilution, comprises a known concentration of distinctly identifiable particles that are loaded with sufficient magnetically responsive material to be captured with substantially total efficiency. The second marker, for determining the magnetic capture efficiency of the target cells, comprises a known concentration of distinctly identifiable particles that are loaded with approximately the same quantity of magnetically-responsive material as the target cell. The second marker can comprise magnetically responsive beads that have been formed with sufficient magnetic material to have a magnetic moment substantially equal to that of the ferrofluid-labeled target entities, and similar fluid transport behavior. Alternatively, the second marker may comprise magnetically inert bodies that are coated with a binding substance having substantially the same number of binding sites and binding affinity as the target cells. Other techniques can be used to provide the second marker with analogous collection behavior relative to the target entity. Such methods are discussed in the following examples.

EXAMPLE 6

Concentration Calibrated Sample Preparation Using Magnetically-Loaded Markers

To 10 ml of blood are added 5 ml of reagent containing an epithelial cell specific ferrofluid, 10,000 green fluorescent 10 μm beads with approximately 500 ferrofluid particles per bead affixed thereto and 10,000 red fluorescent 10 μm beads with approximately 5,000 ferrofluid particles per bead affixed thereto. After 15 minutes of incubation, the sample is placed in a magnetic separator of the type described in U.S. Pat. No. 5,186,827 for 10 minutes. That portion of the sample not attached to the wall of the vessel is discarded, the vessel is removed from the magnetic field and the cells collected on the wall are resuspended in 2 ml of a solution, such as an isotonic buffer or a solution which permeabilizes the cell membrane. The resuspended cells are placed in the magnetic field for 5 minutes and the sample not attached to the wall of the vessel is discarded. The cells collected on the wall are resuspended in 0.2 ml of a solution containing fluorescently labeled antibodies, for example, CD45 PerCP identifying leukocytes, anti EPCAM PE and/or anticytokeratin PE identifying epithelial cells. Optionally, the sample may again be separated, excess antibodies discarded and the collected cells resuspended in a solution containing a nucleic acid dye with fluorescence properties which can be spectrally distinguished from the fluorescence produced by the fluorescent conjugated monoclonal antibodies.

Leukocytes, epithelial cells, green and red beads can then be enumerated by the methods described herein or by traditional enumeration methods. A measurement of, for example, 10 epithelial cells, 5000 green beads and 7000 red beads would indicate that in case the epithelial cells have a density of 500 ferrofluid particles/cell their concentration would be (10×10,000/5000)/10=2 epithelial cells per ml of blood; and in case the epithelial cells have a density of 5,000 ferrofluid particles/cell their concentration would be (10× 10,000/7,000)/10=1.4 epithelial cells per ml of blood.

Although this example describes the use of two makers to accurately determine epithelial cell concentration, it will be apparent that any cell concentration can be determined.

EXAMPLE 7

Sample Preparation Using Ferrofluid-Binding Markers

The cell analysis of Example 6 was repeated, except for the addition of 10,000 red and 10,000 green beads with respectively 500 and 5,000 antigens per bead to the blood. (Many of the antigens are cloned and recombinant proteins can be obtained which are recognized by the antibodies). This is followed by addition of the ferrofluid which identifies both beads and epithelial cells. In this example, an accurate estimate of the absolute number of target cells is obtained and it determines in addition whether the target cell specific ferrofluid works.

Examples 6 and 7, above, describe a sample preparation procedure to control for performance of a cell analysis system, as well as indicate the concentration of the measured target cells per volume unit. An analysis sample prepared according to the procedure described above can then be quantitatively analyzed using flow cytometry, or with the apparatus described herein. The volume in the apparatus described herein is known, whereas the volume which passes through a flow cytometer has to be determined by the beads or by the actual measurement of the volume in which the flow cytometer measured the target events. Using precise sample dispensing techniques (pipette) the volume of the sample, the reagent and the diluent is accurately measured. In the comparable procedure using the apparatus of the present invention, on the other hand, accurate dispensing of sample and reagents is sufficient to determine the cell concentration (without also requiring a count of the beads for volume determination). In its simplest configuration, however, it is desired to obviate precise dispensing of sample. To this end, the bead approach described above can be used to determine the precise dilution of the sample, rather than the determination of the precise volume from which the target cells are analyzed, as exemplified above.

EXAMPLE 8

Cell Concentration Determination Using Calibrated Marker Solution

Approximately 50 μl of a solution containing target cell specific ferrofluid, reagents such as fluorescent nucleic acid dyes to facilitate identification of target cells and a known concentration of 10 μm beads, for example, 1,000 per μl, with physical properties which distinguish them from the target cells, and labeled with an amount of ferrofluid which is in the same range as that of the target cells, are introduced into a separation vessel of the present invention. A drop of blood is also introduced into the vessel by, for example, capillary action. The blood and fluid are mixed and incubated. The vessel is now introduced into a magnetic field and the target cells and beads are aligned along the ferromagnetic lines. From the number of beads counted, the actual volume of blood which was mixed with the fluid can now be determined. For example, if 6,000 beads are measured and the chamber volume is 10 μl, the volume of the marker fluid in the chamber is 6,000/1,000=6 μl. The blood volume in the chamber is thus 10 μl−6 μl=4 μl. If 32,000 target cells are measured, the target cell concentration is 32,000/4=8,000 cells/μl. As should be evident from the foregoing description, neither the exact volume of the blood nor the exact volume of the marker fluid has to be known so long as the concentration of the beads in the marker fluid is known and the blood and bead solution are fully mixed.

As in Example 7, beads can be added which have an amount of antigen which is similar to the amount of antigen on the target cells. In addition to the features described in examples 5, 6, and 7, this procedure further provides a method to determine the efficacy of the techniques and reagents used to select and detect the target material.

C. Assessment of Red Blood Cell Parameters

Important parameters in hematology are hemoglobin and hematocrit, mean corpuscular volume (MCV), mean hemoglobin concentration (MCH), mean cellular hemoglobin concentration (MCHC) and red blood cell number (RBC). To measure erythrocytes, a larger dilution of the blood is required as compared to leukocyte measurements or subsets thereof (on the order of a 1,000 fold higher concentration). A higher fluid volume can be used in the chamber in order to obtain a greater dilution. It also could be advantageous to reduce the chamber height to reduce the number of erythrocytes aligned. Erythrocytes can be identified and aligned by using an erythrocyte specific ferrofluid such as glycophorin A-labeled ferrofluid or transferrin-labeled ferrofluid, the latter recognizing only the immature reticulocytes, i.e., RNA containing erythrocytes. Erythrocytes bound to such ferrofluids can be distinguished from nucleated cells bearing the transferrin receptor by the absence of nuclear fluorescence. Alternatively, one could make use of the presence of hemoglobin in the erythrocytes to render the erythrocytes magnetically responsive. The iron present in hemoglobin can be reduced, or otherwise rendered magnetic according to a known procedure such that the red blood cells will be immobilizable by the internal gradients generated in the vicinity of the ferromagnetic lines. In such a method, no ferrofluid is necessary to attract the erythrocytes to the ferromagnetic lines, and the rate at which they would be attracted toward the ferromagnetic lines would be proportional to the amount of hemoglobin in the cells.

Once the erythrocytes are aligned along the ferromagnetic lines, light scatter and absorption measurements of the individual cells can be performed which permit the assessment of size, volume and hemoglobin content according to procedures for conducting measurements in known hematology analyzers, and suitably adapted for use with the present apparatus.

The ability to assess the shape of the individual erythrocytes provides clinically useful information. Elliptocyte, leptocyte, teardrop rbc, spherocytes, sickle cells, schistocyte, acanthocyte, echinocyte, stomatocyte, xerocyte are all red blood cell shapes associated with disease states which cannot be accurately defined by the assessment of erythrocytes in hematology analyzers. Optionally, the erythrocytes can be further differentiated by the addition of probes which recognize erythrocytes subsets, such as CD71 or transferrin. The fluorescence or other detectable signal of the probe could thus be analyzed through the transparent wall member. Enhancement of the ability to assess red blood cell shapes could be significantly improved by measurement of the surface area of the cell membrane which can be achieved by the addition of a fluorescent membrane dye to the diluent fluid. Measurement of the total amount of fluorescence per cell is then proportional to the total amount of the membrane. From the surface area of the cell membrane and the analysis of the light scatter and fluorescence signals, the shape of the erythrocyte can be derived. The dilution of the blood sample can be determined by the addition of the beads to the diluent fluid, and the number and volume of the erythrocytes can be determined, the hematocrit (volume of cells/(total blood volume)) can also be determined according to the present method.

EXAMPLE 9

Measurement of Immune Status and Function in Whole Blood

One of the critical needs for the immune function is the ability of lymphocytes to re-circulate through the various tissues of the body. This circulation uses blood and lymph for transportation and the antigen receptors present on the lymphocyte surface enable the monitoring of any site where antigen could enter the bloodstream. Memory T cells specific for antigens which are associated with specific infectious diseases such as measles, mumps, tetanus, HIV or Lyme disease are infrequent. However, their number increases dramatically when antigen reenters the body. Monoclonal antibodies specific for disease specific T cells can be made and upon labeling with ferrofluid the antigen (disease)-specific Memory T cells can be aligned and enumerated. Alternately, all specific or subsets of T cells could be aligned. The apparatus of the current invention could then be used to determine specific responses of cell subsets to immunological stimuli.

Sequential flow-by reactions of generic or disease specific antigens or other markers also could be used to determine the functional status and capability among other characteristics of the aligned cells. A particular advantage of the current invention is that the reaction of individual cells can be measured at various time points after stimulation. This type of analysis is an obvious advantage over the measurement of immune function by flowcytometry which permits only on opportunity to measure individual cell responses.

Figure 12:
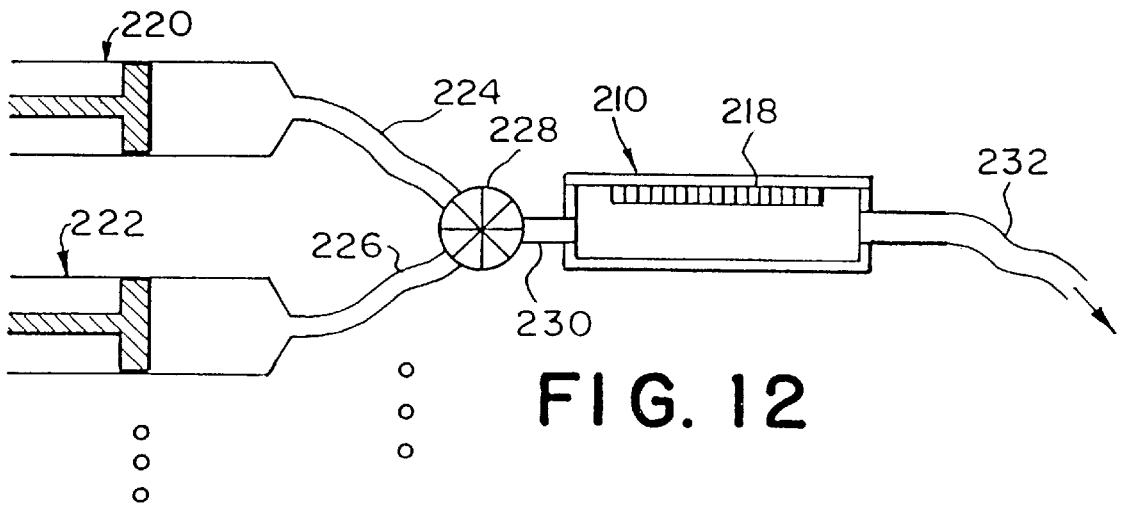
FIG. 12 is a schematic diagram of a separation vessel for use in performing sequential reactions and analysis target material captured therein.

An arrangement for conducting "flow-by" or sequential reactions upon immobilized target material is shown in FIG. 12. Fluid supply means, such as pumps, gravity reservoirs or syringes 220, 222 are provided for containing the test sample and respective reagents for reaction with the target material. Fluid conduits 224, 226 are provided for conducting flows of the respective fluids to a mixing valve 228. The mixing valve 228 is configured to select one or more of the fluid components for mixing and delivery to an inlet port 230 of the separation vessel 210. The separation vessel 210 further includes an outlet port 232 for conducting a flow of fluid out of the separation vessel 210. The separation vessel 210 is configured for use with magnetic arrangements and manual or automatic optical observation means such as have been described above, so that target material may be immobilized therein by a ferromagnetic capture structure 218, and then subjected to sequential reactions with the fluids provided by the fluid supply means and selected by the multi-port valve 228 in sequence and/or combination. In a particularly preferred embodiment, the apparatus in FIG. 12 can be utilized to perform fluorescence in situ hybridization in order to differentiate among characteristics of cell subpopulations. In such a method, the desired types of cells are immobilized in the apparatus. The cell membranes are permeabilized by an appropriate reagent prior to, or after, immobilization. Then, in situ hybridization is performed on the immobilized, permeabilized cells by conducting sequential flows of reagents through the vessel. For fluorescent hybridization, the respective reagents comprise respective fluorescent probes.

The instant invention is particularly well adapted for performing sequential reactions due to the small size of the ferromagnetic lines relative to other internal gradient separators. The lines can be made relatively thin, due to the mechanical support provided by the wall of the vessel. Consequently, cells or other entities are rendered strongly immobilized by the relatively large internal gradients generated in the vicinity of the lines. Such strong immobilization force results in a greater resistance to hydraulic forces incident to conducting flow-by reactions on immobilized substances. Heretofore, magnetic capture structures were of significantly larger dimensions in order to provide an internal gradient with sufficient spatial extent to draw magnetic particles into immobilization. In accordance with the present invention, it has been found that gravitational force and/or an applied external gradient can be employed to draw magnetizable entities toward a strong internal gradient region generated in the vicinity of a capture structure having relatively small dimensions, and supported along one side of the chamber of the separation vessel.

That which is claimed is:

1. An.apparatus for observing magnetically-reponsive microscopic entitities suspended in a fluid medium, comprising:

a vessel having a transparent wall and a chamber formed therein for containing the fluid medium;

a ferromagnetic capture structure lithographically formed on the transparent wall; and magnetic means for inducing an internal magnetic gradient in the vicinity of the ferromagnetic capture structure, whereby the magnetically-responsive entities are immobilized along the wall adjacent to the capture structure.

2. The apparatus of claim 1 wherein the vessel comprises a fluid inlet and a fluid outlet for conducting a flow of fluid through the vessel.

3. The apparatus of claim 2 comprising fluid supply means connected with the fluid inlet for sequentially supplying a plurality of reagents to the fluid inlet.

4. The apparatus of claim 2 wherein the ferromagnetic capture structure comprises a plurality of ferromagnetic lines having an effective diameter of less than 30 μm.

5. The apparatus of claim 4 wherein the magnetic means is configured to apply an external gradient to the vessel for transporting entities within the vessel in the direction of the capture structure.

6. The apparatus of claim 5, comprising an automated optical observation system for detecting and enumerating the immobilized entities.

7. The apparatus of claim 6 wherein the automated observation system comprises:

an optical detector for detecting said immobilized entities; and tracking means for scanning the optical detector parallel to the ferromagnetic lines.

8. The apparatus of claim 7 wherein the vessel comprises a fluid inlet and a fluid outlet for conducting a flow of fluid through the vessel.

9. The apparatus of claim 8 comprising fluid supply means connected with the fluid inlet for sequentially supplying a plurality of reagents to the fluid inlet.

10. An apparatus for observing magnetically-reponsive microscopic entitities suspended in a fluid medium, comprising:

a vessel having a transparent wall and a chamber formed therein for containing the fluid medium;

a ferromagnetic capture structure supported on the transparent wall;

magnetic means for inducing an internal magnetic gradient in the vicinity of the ferromagnetic capture structure, whereby the magnetically-responsive entities are immobilized along the wall adjacent to the capture structure; and an automated optical observation system for detecting and enumerating the immobilized entities;

wherein the automated observation system comprises:
an optical detector for detecting said immobilized entities; and
optical tracking means for scanning the optical detector along the capture structure.

11. The apparatus of claim 10 wherein the automated observation system comprises a vibratable support for supporting and selectively vibrating the vessel.

12. The apparatus of claim 11 wherein the vibratable support comprises a piezoelectric vibrator.

13. An apparatus for observing magnetically-reponsive microscopic entitities suspended in a fluid medium, comprising:

a vessel having a transparent wall and a chamber formed therein for containing the fluid medium;

a ferromagnetic capture structure supported on the transparent wall;

magnetic means for inducing an internal magnetic gradient in the vicinity of the ferromagnetic capture structure, and for applying an external gradient perpendicular to the ferromagnetic capture structure, whereby the magnetically-responsive entities are transported toward and immobilized along the wall adjacent to the capture structure.

14. The apparatus of claim 13 wherein the magnetic means comprises a pair of magnets having tapered pole surfaces positioned to provide a gap therebetween for receiving the vessel.

15. The apparatus of claim 13 wherein the ferromagnetic capture structure comprises a plurality of ferromagnetic lines having an effective diameter of less than 30 Am.

16. The apparatus of claim 15 wherein the ferromagnetic lines are supported on the wall by adhesion.

17. The apparatus of claim 16 wherein the ferromagnetic lines are lithographically formed on the wall.

18. A method of immobilizing microscopic magnetically-responsive entities suspended in a fluid medium for observation, comprising the steps of:

providing a vessel having a chamber with a transparent wall and a ferromagnetic capture structure supported on the wall;

introducing the fluid medium into the chamber;

applying a magnetic field to the chamber to induce an internal magnetic gradient in the vicinity of the ferromagnetic capture structure;

immobilizing the magnetically-responsive entities in a line against the transparent wall and adjacent to the ferromagnetic capture structure; and observing the magnetically responsive entities held against the wall adjacent to the ferromagnetic capture structure.

19. The method of claim 18 wherein the ferromagnetic capture structure comprises a plurality of linear ferromagnetic elements, and said observing step comprises the step of scanning along the linear ferromagnetic elements with an automated optical detection system.

20. The method of claim 18 wherein said observing step comprises the step of enumerating the magnetically responsive entities.

21. The method of claim 18 wherein said applying step comprises the step of orienting the vessel to position the ferromagnetic capture structure beneath the chamber such that the magnetically responsive entities are transported toward the capture structure under the influence of gravity.

22. The method of claim 18 wherein the applying step comprises applying an external magnetic gradient to the vessel to transport the magnetically-responsive entities toward the capture structure.

23. The method of claim 22 wherein the ferromagnetic capture structure comprises a plurality of linear ferromagnetic elements, and said observing step comprises the step of scanning along the linear ferromagnetic elements with an automated optical detection system.

24. A method of immobilizing microscopic magnetically-responsive entities suspended in a fluid medium for observation, comprising the steps of:

providing a vessel having a chamber with a transparent wall and a ferromagnetic capture structure supported on the wall;

introducing the fluid medium into the chamber;

applying a magnetic field having an external gradient to the chamber to induce an internal magnetic gradient in the vicinity of the ferromagnetic capture structure and to transport magnetically-responsive entities toward the capture structure;

collecting said magnetically-responsive entities in a linear monolayer against the wall and adjacent to the ferromagnetic capture structure; and observing the magnetically responsive entities held against the wall adjacent to the ferromagnetic capture structure.

25. A method of immobilizing microscopic magnetically-responsive entities suspended in a fluid medium for observation, comprising the steps of:

provising a vessel having a chamber with a transparent wall and a ferromagnetic capture structure supported on the wall;

introducing the fluid medium into the chamber;

applying a magnetic field to the chamber to induce an internal magnetic gradient region in the vicinity of the ferromagnetic capture structure;

applying a transport force to entities located in the chamber substantially out of range of the internal magnetic gradient region to transport magnetically-responsive entities toward the internal magnetic gradient region;

collecting said magnetically-responsive entities in a linear monolayer against the wall and adjacent to the ferromagnetic capture structure for substantialy unobstructed observation through the wall; and observing the magnetically responsive entities through the transparent wall against the wall adjacent to the ferromagnetic capture structure.

26. The method of claim 25, wherein the step of applying the transport force comprises the step of orienting the chamber to employ gravity as the transport force for transporting the entities toward the internal magnetic gradient region.

27. The method of claim 25 wherein the step of applying the transport force comprises the step of applying an external magnetic gradient to the chamber.

28. The method of claim 27 wherein the external magnetic gradient is applied to transport the entities in a direction contrary to the influence of gravity.

* * * * *